United States Patent [19]

Lynch

[11] Patent Number: 5,229,115
[45] Date of Patent: Jul. 20, 1993

[54] ADOPTIVE IMMUNOTHERAPY WITH INTERLEUKIN-7

[75] Inventor: David H. Lynch, Bainbridge Island, Wash.

[73] Assignee: Immunex Corporation, Seattle, Wash.

[21] Appl. No.: 559,001

[22] Filed: Jul. 26, 1990

[51] Int. Cl.⁵ .................... A61K 35/14; A61K 37/02; C12N 5/08
[52] U.S. Cl. .................. 424/93 V; 435/240.2; 435/70.1; 424/85.2; 424/534
[58] Field of Search .................. 435/240.1, 70.1; 424/93, 534, 85.2, 93 V

[56] References Cited

U.S. PATENT DOCUMENTS

| | | | |
|---|---|---|---|
| 4,902,288 | 2/1990 | Ingram | 424/534 |
| 4,965,195 | 10/1990 | Namen et al. | 435/240.2 |
| 5,032,396 | 7/1991 | Williams | 530/351 |
| 5,041,289 | 8/1991 | Philips et al. | 435/240.2 |

OTHER PUBLICATIONS

Matis et al., J. Immunol. vol. 136(9), May 1986 pp. 3496–3501.
Rosenberg, S. A. Adoptive Immunotherapy for Cancer. Scientific American, pp. 62–69, May, 1990.
Parmiani, G. An Explanation of the Variable Clinical Response to Interleukin-2 and LAK Cells. *Immunology Today* 11:113, 1990.
Widmer, M. B. et al., Regulation of Cytolytic Cell Population from Human Peripheral Blood by B Cell Stimulatory Factor 1 (Interleukin-4). *J. Exp. Med.* 166: 1447; 1986.
Kawakami, Y. et al. Interleukin-4 Promotes the Growth of Tumor-Infiltrating Lymphocytes Cytotoxic for Human Autologous Melanoma. *J. Exp. Med.* 168: 2183; 1988.
Mulé, J. J. et al. IL-4 Regulation of Murine Lymphokine-Activated Killer Activity In Vitro. *J. Immunol.* 142: 726; 1989.
Namen, A. E. et al. B Cell Precursor Growth-promoting Factor. *J. Exp. Med.* 167: 988; 1988.
Namen, A. E. et al. Stimulation of B-Cell Progenitors by Cloned Murine Interleukin-7. *Nature* 333: 571; 1988.
Cosman, D. et al. Interleukin-7: A Lymphoid Growth Factor Active on T and B Cell Progenitors. In *Lymphokine Receptor Interactions* 179: 229. INSERM/John Libbey Eurotext LTD, 1989.
Lee, G. et al. Normal B Cell Precursors Responsive to Recombinant Murine IL-7 and Inhibition of IL-7 Activity by Transforming Growth Factor-$\beta$. *J. Immunol.* 142: 3875; 1989.
Takeda, S. et al. In Vitro Effects of Recombinant Interleukin-7 on Growth and Differentiation of Bone Marrow Pro-B and Pro-T-Lymphocyte Clones and Fetal Thymocyte Clones. *Proc. Natl. Acad. Sci.* (USA) 86: 1634; 1989.
Hayashi, S. et al. Stepwise Progression of B Lineage Differentiation Supported by Interleukin-7 and Other Stromal Cell Molecules. *J. Exp. Med.* 171: 1683; 1990.
Everson, M. P. et al. Synergism of Interleukin 7 with Thymocyte Growth Factors Interleukin 2, Interleukin 6 and Tumor Necrosis Factor $\alpha$ in the Induction of Thymocyte Proliferation. *Cellular Immunol.* 127: 470; 1990.
Conlon, P. J. et al. Murine Thymocytes Proliferate in Direct Response to Interleukin-7. *Blood* 74: 1368; 1989.

(List continued on next page.)

*Primary Examiner*—Jacqueline Stone
*Attorney, Agent, or Firm*—Patricia Anne Perkins; Christopher L. Wight

[57] ABSTRACT

There is disclosed an immunotherapy method for treating an individual with cancer or a viral infection comprising obtaining lymphoid cells previously exposed to a specific antigen, culturing the lymphoid cells ex vivo in a culture medium containing an effective amount of an IL-7 polypeptide or a functional derivative thereof to induce CTL activity in the lymphoid cells and administering the lymphoid cells having CTL activity for cells displaying the specific antigen to an individual.

31 Claims, 19 Drawing Sheets

OTHER PUBLICATIONS

Morrissey, P. J. et al. Recombinant Interleukin 7, Pre-B Cell Growth Factor, has Costimulatory Activity on Purified Mature T Cells. *J. Exp. Med.* 169: 707; 1989.

Chazen, G. D. et al. Interleukin 7 is a T-Cell Growth Factor. *Proc. Natl. Acad Sci.* (USA) 86: 5923; 1989.

Chantry, D. et al. Interleukin 7 (Murine Per-B Cell Growth Factor/Lymphopoietin 1) Stimulates Thymocyte Growth: Regulation by Transforming Growth Factor Beta. *Eur. J. Immunol.* 19:783; 1989.

Watson, J. D. et al. Effect of IL-7 on the Growth of Fetal Thymocytes in Culture. *J. Immunol.* 143: 1215; 1989.

Okazaki, H. et al. IL-7 Promotes Thymocyte Proliferation and Maintains Immunocompetent Thymocytes Bearing $\alpha\beta$ or $\gamma\delta$ T-Cell Receptors in Vitro: Synergism with IL-2. *J. Immunol.* 143: 2917; 1989.

Londei, M. et al. Interleukin 2 is a Growth Factor for Mature Human T Cells. *Eur. J. Immunol.* 20:425; 1990.

Armitage, R. J. et al. Regulation of Human T Cell Proliferation by IL-7. *J. Immunol.* 144: 938; 1990.

Grabstein, K. H. et al. Regulation of T Cell Proliferation by IL-7. *J. Immunol.* 144: 3015; 1990.

Welch, P. A. et al. Human IL-7: A Novel T Cell Growth Factor. *J. Immunol.* 143: 3562; 1989.

Suda, T. et al. Growth Promoting Activity of IL-1a, IL-6, and Tumor Necrosis Factor-a in combination with IL-2, IL-4, or IL-7 on Murine Thymocytes. *J. Immunol.* 144: 3039; 1990.

Lynch, D. H. et al. IL-7 Induces LAK Activity in Resting Murine T Cells. Abstract, FASEB meeting, Jun. 4–7, 1990.

Henney, C. S. Interleukin 7: Effects on Early Events in Lymphopoiesis. *Immunology Today* 10: 170; 1989.

Cytokine(s) Added to Culture Medium
FIG. 17A   IL-2(5 ng/ml)
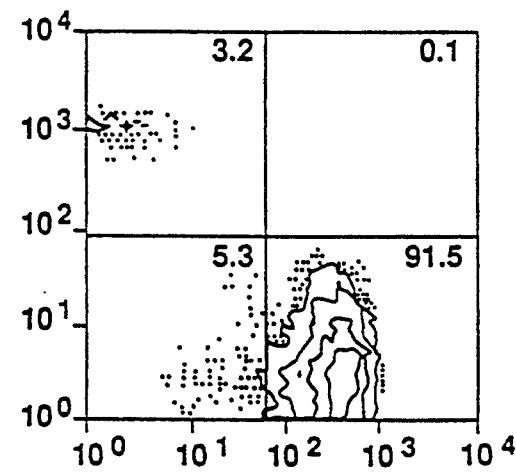
FIG. 17B   IL-7(10 ng/ml)
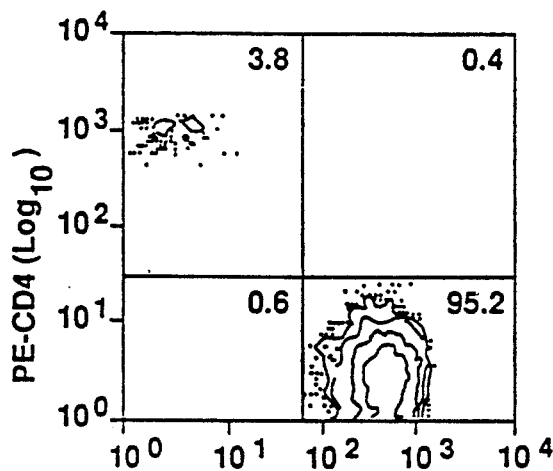
FIG. 17C   IL-7(10 ng/ml)
+
IL-2(2 ng/ml)
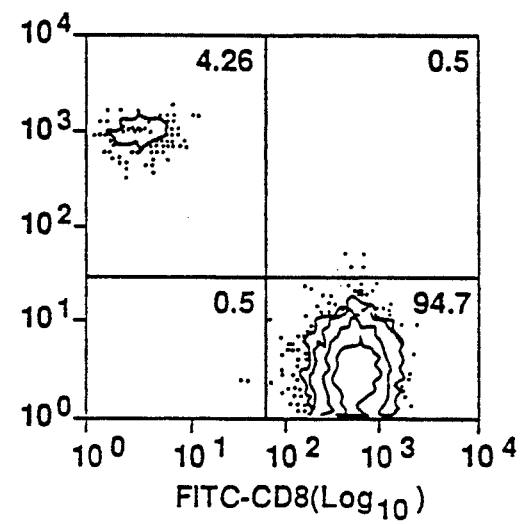

ADOPTIVE IMMUNOTHERAPY WITH INTERLEUKIN-7

TECHNICAL FIELD OF THE INVENTION

The present invention relates to a method for adoptive immunotherapy for treating an individual with cancer or a viral infection comprising obtaining a sample of peripheral lymphoid cells previously exposed to a specific antigen, culturing the lymphoid cells ex vivo in a culture medium containing an Interleukin-7 (IL-7) polypeptide or a derivative thereof at a concentration sufficient to activate CTL activity in the lymphoid cells, and administering the activated lymphoid cells to the individual.

BACKGROUND OF THE INVENTION

The in vitro cell culture of resting lymphoid cells from normal mice with either Interleukin-2 (IL-2) or Interleukin-4 (IL-4) has been shown to generate populations of lymphoid cells which are cytotoxic to tumor cells. These cells are generally referred to as lymphokine-activated killer (LAK) cells. IL-2 and IL-4 are distinct T cell derived cytokines or, more particularly, lymphokines. Both IL-2 and IL-4 have been shown to have some overlapping activities. For example, IL-2 was initially identified as a T cell growth factor, but has since been shown to bind to and promote propagation or function of such diverse cell types as B cells, monocytes, epidermal Langerhans cells, oligodendroglial cells and NK cells. Moreover, IL-4 was originally thought to function primarily by inducing B cell proliferation and maturation, IL-4 has since been shown to interact with hematopoietic stem cells, macrophages, mast cells, and T cells.

Mammalian Interleukin-7 (IL-7) had been previously designated lymphopoietin-1. The cloning and expression of human and mouse IL-7 has been described in U.S. Pat. No. 4,965,195 and the disclosure of which is incorporated by reference herein. Interleukin-7 is a lymphopoietic growth factor that was first isolated and cloned by virtue of its ability to stimulate the growth of B and T cell progenitors in bone marrow. Published PCT Application WO89/03884 (May 5, 1989) and EP-A-0314415 (May 3, 1989) refer to DNAs, vectors, and related processes for producing mammalian IL-7 polypeptides by recombinant DNA technology. The relevant disclosures of these published patent applications are incorporated by reference herein. The cloning of murine IL-7 was first reported in the scientific literature by Namen et al., *Nature* 333:571 (1988) and human IL-7 by Goodwin et al., *Proc. Natl. Acad. Sci. USA* 86:302 (1989). Purification of murine IL-7 from supernatants of transformed bone marrow stromal cell lines indicated an apparent molecular weight of approximately 25,000 daltons (see, for example, Namen et al., *J. Exp. Med.* 167:988 (1988)). The cloned DNAs reported by Namen et al. and Goodwin et al. suggest minimum molecular weights for the murine and human IL-7 polypeptides of 14,897 and 17,387 daltons, respectively, exclusive of any glycosylation.

Cloning, characterization and expression of sufficient quantities of IL-7 has provided sufficient recombinant polypeptide to begin characterizing its spectrum of its biological activities. IL-7 was originally defined by its ability to stimulate the proliferation of pre-B cells (B220+) derived from long-term bone marrow culture (see, Whitlock et al., *J. Immunol. Methods* 67:353-69 (1984)). IL-7 was unable, however, to stimulate the proliferation of mature B cells or to induce the differentiation of pre-B cells to surface Ig+ cells (Lee et al., *J. Immunol.* 142:3875-83 (1989)).

More recent references have shown that T cell lineage cells respond to IL-7. For example, resting fetal and adult thymocytes of most surface phenotypes proliferate in response to IL-7 in a manner independent of IL-2, IL-4, or IL-6 (Conlon et al., *Blood* 74:1368-73 (1989)). Further, mature peripheral T cells respond to IL-7 in the presence of suboptimal mitogen concentrations (Chazen et al., *Proc. Natl. Acad. Sci. USA* 86:5923-27 (1989)). Morrissey et al., *J. Exp. Med.* 169:707-16 (1989) have shown that IL-7 can provide a costimulatory signal for the in vitro proliferative response of purified murine T cells to CON A by inducing IL-2 production. Additionally, Chazen et al., *Proc. Natl. Acad. Sci. USA* 86:5923-27 (1989) have further shown that IL-7 in combination with PMA, can directly stimulate T cell activation without intervention by another cytokine messenger. Response to a combination of IL-7 and PMA was not inhibited by high concentrations of neutralizing antibodies to either IL-2 or IL-4 and was largely resistant to immunosuppressive effects of CsA, a drug which inhibits the transcription of a number of lymphokine genes, including those encoding IL-2, IL-4 and interferon-γ.

A wide spectrum of murine cell lines and primary cell lines display IL-7 receptors. These cell lines include cells of both lymphoid and myeloid origin. Therefore, the cytokine IL-7 has the potential for a wide range of activities on a wide variety of cell types.

The differentiation of lymphoid lineage cells involves a complex and as yet poorly understood series of events. Although a common precursor, or stem cell, is believed to give rise to both B and T lymphocytes, the steps involved in the differentiation process have remained elusive. Early CD4-/CD8- thymocytes can repopulate the thymus of irradiated recipients and differentiate into various thymocyte subpopulations. It is not known what factors are involved in the differentiation process.

Conlon et al., *Blood* 74:1368-73 (1989) refers to a proliferative response of murine thymocytes to murine IL-7. IL-7 alone was mitogenic for thymocytes and further augmented an IL-7 response with CON A. Conlon et al. further demonstrated that IL-7 stimulated the proliferation of CD4-/CD8- cells that represent what is believed to be the least differentiated thymocyte subpopulation. Moreover, the response of thymocytes to IL-7 did not appear to be due to the production of other known T cell growth factors, such as IL-2 and IL-4. This IL-7 activity is in contrast to other lymphokine activities, such as IL-1 or IL-6, which have been shown to enhance T cell responsiveness by either the production of IL-2, IL-4, or by upregulation of the IL-2 receptor, or both.

The technique of adoptive immunotherapy and its various modifications are described, for example, in Rosenberg, *Scientific American*, pp. 62-69 (May, 1990). The adoptive immunotherapy model was first developed using IL-2. The procedure was developed in mice. Briefly, one first removes the spleen from a healthy syngeneic mouse, isolates the lymphocytes and cultures the isolated lymphocytes in a culture medium containing IL-2. IL-2 induces certain lymphoid cells and NK cells in culture to become cytolytic and tumorcidal. The activated lymphocytes and IL-2 are injected into tumor-bearing mice as a method of immunotherapy of cancer. Human clinical studies have isolated lymphocytes from whole blood of the patient, activated the lymphocytes in culture with IL-2 to induce LAK activity, and treated the patients with about 50 billion LAK cells infused intravenously together with human IL-2. Various clinical studies found the necessity of infusing IL-2 together with the activated lymphocytes.

Rosenberg and his colleagues have attempted to treat various cancers with activated LAK cells in combination with IL-2 and with IL-2 administered alone. Their results to date have shown complete cancer remission in 14 of 177 patients with the combination of activated LAK cells plus IL-2 and in 4 of 130 cancers with IL-2 alone. When partial remission cases are considered, 25% of the patients who received activated LAK cells plus IL-2 improved and 17% of the patients who received IL-2 alone improved. These studies are ongoing.

There have been reported side effects with the adoptive immunotherapy technique with lymphocytes activated by IL-2 and administered concomitantly with IL-2. The side effects include proliferation of lymphocytes in tissues that interfere with the function of vital organs. Administration of IL-2 leads to leakage of fluid from blood into tissues with resultant weight gain.

Therefore, there is a need in the art to better characterize the precise physiologic and immunologic functions of IL-7 polypeptides. There is a further need in the art to improve upon immunotherapeutic techniques with different cytokines under different exposure conditions, different combinations and different pharmacokinetics parameters. This invention was made in an effort to find an optimal immunotherapeutic use for IL-7 polypeptides alone or in combination with other cytokines or other factors.

SUMMARY OF THE INVENTION

The present invention relates to a method for treating an individual with cancer or a viral infection by adoptive immunotherapy with CTLs (cytolytic T lymphocytes) activated in the presence of an IL-7 polypeptide or a derivative thereof. The method comprises obtaining syngeneic peripheral lymphoid cells previously exposed to a tumor cell population or a virus infection (i.e., specific antigen), culturing the lymphoid cells ex vivo in a culture medium containing an amount of a conspecific IL-7 polypeptide or a derivative thereof sufficient to induce CTL activity in the lymphoid cells, and administering the lymphoid cells displaying CTL activity to the individual. Preferably, the culture medium further comprises up to about 3 ng/ml of a conspecific IL-2 polypeptide or a derivative thereof and/or up to about 10 ng/ml of a conspecific IL-4 polypeptide or a derivative thereof.

Preferably, the syngeneic peripheral lymphoid cells are obtained from a draining lymph node adjacent to a tumor or a virally-infected site. Most preferably, in a human individual, autologous lymph cells are used. Autologous lymph cells are obtained from the same individual who is later treated with the cells.

Cytolytic T lymphocytes (CTL) cells, activated by ex vivo culture with either IL-7 alone or a combination of IL-7 plus IL-2, can be used for adoptive immunotherapy of cancer with lytic activity specific for tumor cells. Moreover, it is possible to further add mitotically-inactivated tumor cells to the ex vivo culture to enhance CTL activity of the cells.

The step of administering the lymphoid cells displaying CTL activity to the individual may further comprise administering a cytokine to the individual, wherein the cytokine is selected from the group consisting of an IL-7 polypeptide or a derivative thereof, a combination of an IL-7 polypeptide or a derivative thereof in combination with an IL-2 polypeptide or a derivative thereof or an IL-4 polypeptide or a derivative thereof, and a combination of an IL-7 polypeptide or a derivative thereof, and an IL-2 polypeptide or a derivative thereof, an IL-4 polypeptide or a derivative thereof. Preferred daily dosages for administration of cytokines include from about 10 to about 2000 µg/kg/day for IL-2, from about 4 to about 1000 µg/kg/day for IL-4 and IL-7. Most preferably, the daily dose of IL-2 is administered each day in three separate doses and IL-4 and IL-7 are each administered twice daily (bid).

One can obtain a population of syngeneic lymphocytes for adoptive immunotherapy of cancer. The population of syngeneic lymphocytes are obtained from peripheral lymphoid cells, preferably peripheral lymphoid cells that are draining a particular tumor site. The syngeneic peripheral lymphoid cells are cultured ex vivo in an amount of conspecific IL-7 polypeptide or derivative thereof sufficient to induce CTL activity in the lymphoid cells, wherein the CTL activity is characterized by CD8 positive T cells. Preferably, the culture medium further comprises up to about 3 ng/ml of a conspecific IL-2 polypeptide or derivative thereof and/or an IL-4 polypeptide or a derivative thereof and possibly mitotically-inactivated tumor cells.

The present invention further comprises a population of proliferated and activated cytolytic T lymphocytes having lytic specificity for target cells (e.g., tumor cells or virally-infected cells) displaying a specific antigen. The inventive cells are produced ex vivo by a process comprising obtaining syngeneic peripheral lymphoid cells previously exposed to a tumor cell population or a virus infection, and culturing the lymphoid cells ex vivo in a culture medium containing an amount of a conspecific IL-7 polypeptide or a derivative thereof sufficient to induce CTL activity in the lymphoid cells. The inventive cells are useful for adoptive immunotherapy of cancers and viral infections. The inventive cells are further characterized by a population of CD8 positive T cells and substantially lacking NK cells. Preferably, the culture medium further comprises up to about 3 ng/ml of a conspecific IL-2 polypeptide or derivative thereof and possibly mitotically-inactivated specific tumor cells. Preferably, the amount of IL-7 polypeptide or equipotent or active derivative thereof present in the culture medium is from about 2.5 ng/ml to about 20 ng/ml. Most preferably, the amount of IL-7 polypeptide or equipotent or active derivative thereof is about 10 ng/ml.

BRIEF DESCRIPTION OF THE DRAWINGS

FIG. 5 illustrates the lytic activity of groups of DLN or CLN cells that were cultured without cytokine or in the presence of 2 ng/ml of IL-2. These data show that DLNs have superior lytic activity to CLNs and that DLNs incubated with IL-2 had the best lytic activity of this group.

FIG. 6 compares mean tumor size of 1024 tumor injected in C3H mice. The mice received varying therapeutic concentrations of CLNs or DLNs that were previously incubated either with 2 ng/ml of IL-2 or without cytokine. These data show that DLN cells had superior anti-tumor activity to CLN cells. The presence of IL-2 in the medium of DLN cells did not significantly enhance the anti-tumor activity of DLN cells.

FIG. 7 shows the lytic activity of DLNs and CLNs incubated either with 2 ng/ml of IL-7 or a combination of 2 ng/ml of IL-2 plus 10 ng/ml of IL-7. These data show the superior lytic activity of DLNs incubated in the presence of 2 ng/ml IL-7 as compared with DLN's cultured in the absence of added cytokines.

FIG. 8 depicts a comparison of in vivo anti-tumor activity of various cells that have been incubated with IL-7 or a combination of IL-2 plus IL-7. Mean tumor size was compared at several days post tumor challenge. These data illustrate that DLNs incubated with IL-7 demonstrated superior tumoricidal activity when compared with DLNs incubated in the absence of added cytokine or CLNs incubated with IL-7 or a combination of IL-2 and IL-7.

FIG. 9 compares the lytic activity of DLNs and CLNs incubated either without cytokine or in the presence of IL-7 at a concentration of 10 ng/ml. DLNs incubated with IL-7 demonstrated superior lytic activity in this in vitro model.

FIG. 10 compares in vivo tumoricidal activity of DLNs and CLNs incubated without cytokine or in the presence of 10 ng/ml IL-7. Superior tumoricidal activity to the point of complete tumor cure was evidenced by $6 \times 10^6$ DLN cells injected into C3H mice after the DLNs were incubated for four days in the presence of 10 ng/ml of IL-7.

FIG. 11 depicts data comparing in vitro lytic activity of DLNs and CLNs incubated either without the presence of cytokines or in the presence of 20 ng/ml of IL-7 or 2 ng/ml of IL-2 plus 10 ng/ml of IL-7. Superior lytic activity was evidenced by DLNs incubated in the presence of the higher concentration of IL-7.

FIG. 12 illustrates in vivo data comparing tumoricidal activity of DLNs and CLNs incubated either without cytokine or in the presence of 20 ng/ml of IL-7. Superior tumoricidal activity was obtained with DLNs incubated with IL-7.

FIG. 13 shows in vitro lytic activity to be superior with DLNs incubated with 2 ng/ml of IL-2 plus 10 ng/ml of IL-7.

FIG. 14 shows data comparing in vivo tumoricidal activity of various DLNs and CLNs. DLNs incubated in the presence of a combination of IL-2 plus IL-7 had the best anti-tumor activity.

FIGS. 15–18 depict data from an experiment comparing in vivo anti-tumor activity and in vitro lytic activity of DLNs and CLNs maintained in long term culture conditions that included cytokine supplementation. The cells could not have been maintained under long term culture conditions without cytokine supplementation, because lymphoid cells die off in approximately one week without cytokine supplementation of the culture medium. The long term cultures may further include irradiated specific tumor cells (B10.5 cells irradiated with 2000 rads of gamma irradiation).

FIG. 15 depicts a comparison of in vivo anti-tumor activities of DLNs and CLNs. These data show that only specific tumor (B10.5) and not a non-cross-reactive tumor (B10.2) could be removed by short term cultures of DLNs previously exposed to specific (B10.5) tumor.

FIG. 16 shows in virtro lytic activity of long term (five week) cultures of DLN cells with the indicated cytokine. Specific lytic activity was shown against specific B10.5 tumor cells rather than nonspecific B10.2 tumor cells.

FIG. 17 A-C shows flow cytometric analysis of DLN cells maintained under long term culture conditions with the indicated cytokine. DLN cells maintained with IL-7 became a population of predominantly CD8 positive T cells.

FIG. 18 shows in vivo anti-tumor data for DLNs maintained in long term culture conditions with the indicated cytokine. DLN cells cultured long term in medium containing IL-7 were immunotherapeutically effective at eliminating specific (B10.5) tumor challenge, but not non-specific (B10.2) tumor challenge.

FIG. 19 A–C shows photographs of the same mouse DLN cells after 9 weeks in parallel culture.

DETAILED DESCRIPTION OF THE INVENTION

Figure 1:
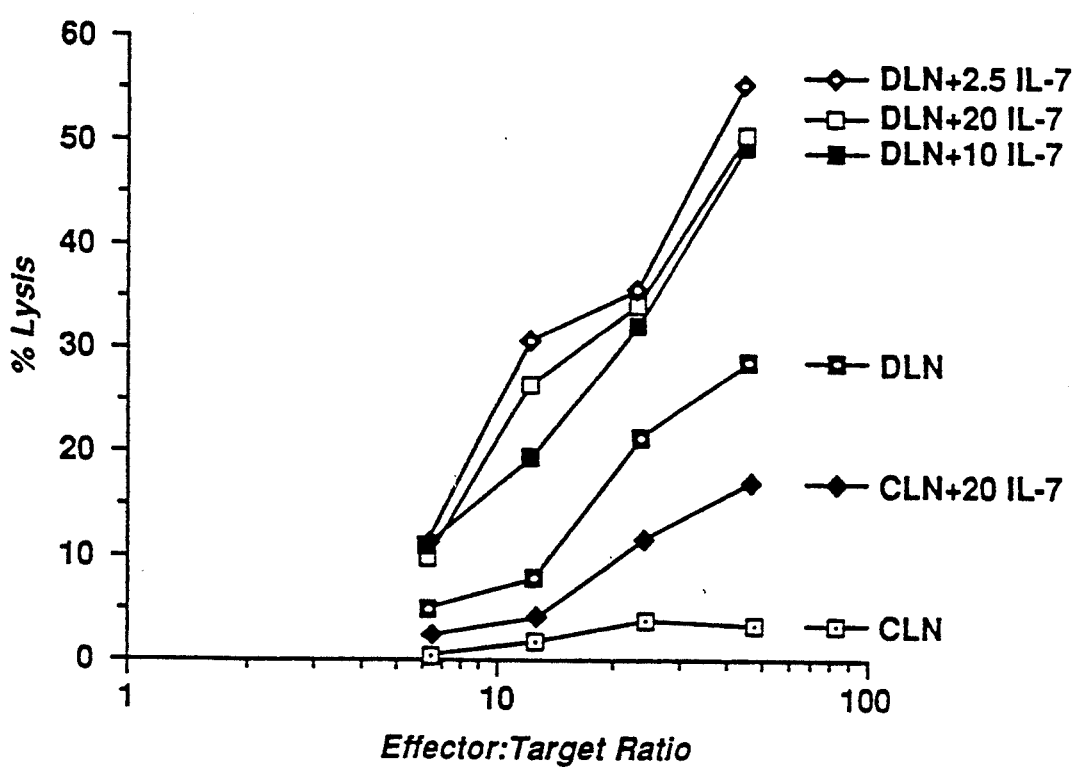
FIG. 1 illustrates a comparison of various effector to target ratio cell titrations for draining lymph node cells (DLN) or control lymph node cells (CLN) cultured in in either in 2.5, 10, or 20 ng/ml of IL-7 or without IL-7 (control) in the medium. The data compare the percent lysis of 1024 tumor cells when treated in vitro with control CLNs, CLNs incubated with 20 ng/ml IL-7, control DLN, or DLNs incubated with 2.5, 10, or 20 ng/ml of IL-7. These data indicate the highest amount of lysis for a given effector cells to target cells is achieved when the DLNs are incubated in IL-7.

The present invention relates to a method for forming a population of activated mammalian cytolytic T lymphocytes having lytic activity for cells displaying a specific antigen, comprising contacting a T cell population previously exposed to the specific antigen with a biologically effective quantity of an IL-7 polypeptide or a derivative thereof. Preferably, the mammalian cytotoxic T lymphocytes are human cells and are obtained from a peripheral draining lymph node that drains a tumor site, such as a solid tumor, or drains a virally-infected site. Draining lymph node cells contain a population of T lymphocyte cells previously exposed to the specific antigen. The specific antigen is displayed on tumor cells or virally infected cells, or by the virus.

The population of mammalian cytotoxic T lymphocytes needs previous exposure to the specific antigen displayed by the virus, virally infected mammalian cells, or tumor cells. A draining lymph node downstream (by blood circulation or lymph drainage) from a site of tumor growth or viral infection will contain DLN (draining lymph node) cells. DLN cells are activated ex vivo by the inventive process. Syngeneic CLN (control lymph node) cells, without previous exposure to the specific antigen, will be less effective after ex vivo activation with an IL-7 polypeptide or a derivative thereof according to the inventive method. CLN cells can serve as an experimental control for cells not previously exposed to the specific antigen.

Mammalian cytolytic T lymphocytes previously exposed to the specific antigen are preferably obtained from a draining lymph node. It is also possible to obtain peripheral blood lymphocytes that have been exposed to a specific antigen. For purposes of this disclosure, any mammalian T lymphocyte previously exposed to a specific antigen, irrespective of where or how it was obtained, will be considered a DLN cell previously exposed to the specific antigen.

DLN cells are proliferated in ex vivo culture by being incubated in a culture medium comprising a biologically effective amount of an IL-7 polypeptide or a derivative thereof. The culture medium may further comprise up to about 3 ng/ml of an IL-2 polypeptide or a derivative thereof, and/or a population of mitotically inactivated specific tumor cells displaying the specific antigen. The tumor cells may be mitotically inactivated, for example, by irradiation with at least about 500 rads of gamma irradiation, preferably about 2000 rads of gamma irradiation. Other amount and forms of irradiation may also effectively mitotically inactivate tumor cells such that they become incapable of cell division, but are still metabolically active. Another means to mitotically inactivate specific tumor cells is to treat them with a chemical agent, such as Mitomycin C.

The culture medium comprises an IL-7 polypeptide or a derivative thereof. For use in accordance with the present invention, IL-7 can be produced by any convenient method, for example by expression in a mammalian cell line or in a prokaryote, as described by methods known in the art. The IL-7 polypeptide or derivative thereof should be conspecific, meaning having an amino acid sequence substantially similar to IL-7 polypeptides for the particular species who will receive the activated DLN cells. This means that for human use, the IL-7 polypeptide or other cytokine should have a substantially human sequence so as to minimize recognition of the cytokine as a foreign substance.

The amino acid sequences for human and murine IL-7s are set forth in Tables 1 and 2, below:

TABLE 1

Human IL-7

| GLY | LYS | ASP | GLY | LYS | GLN | TYR | GLU | SER | VAL | ASP | CYS | ASP | ILE | GLU | 5 |
|---|---|---|---|---|---|---|---|---|---|---|---|---|---|---|---|
| ASP | GLN | LEU | LEU | ASP | SER | MET | LYS | GLU | ILE | LEU | MET | VAL | SER | ILE | 20 |
| ASN | ASN | GLU | PHE | ASN | PHE | PHE | LYS | ARG | HIS | GLY | SER | ASN | CYS | LEU | 35 |
| LYS | GLU | GLY | MET | PHE | LEU | PHE | ARG | ALA | ALA | ILE | CYS | ASP | ALA | ASN | 50 |
| PHE | LEU | LYS | MET | ASN | SER | THR | GLY | ASP | PHE | ARG | LYS | LEU | ARG | GLN | 65 |
| LYS | VAL | SER | GLU | GLY | THR | THR | ILE | LEU | LEU | ASP | LEU | HIS | LEU | LEU | 80 |
| VAL | LYS | GLY | ARG | LYS | PRO | ALA | ALA | LEU | GLY | ASN | CYS | THR | GLY | GLN | 95 |
| LYS | SER | LEU | GLU | GLU | ASN | LYS | SER | LEU | LYS | GLU | ALA | GLN | PRO | THR | 110 |
| ASN | ASP | LEU | CYS | PHE | LEU | LYS | ARG | LEU | LEU | GLU | GLN | LYS | LYS | LEU | 125 |
| CYS | TRP | ASN | LYS | ILE | LEU | MET | GLY | THR | LYS | GLN | GLU | ILE | LYS | THR | 140 |
|  |  |  |  |  |  |  |  |  |  | HIS |  |  |  |  | 152 |

TABLE 2

Murine IL-7

| ASP | LYS | GLU | GLY | LYS | ALA | TYR | GLU | SER | VAL | GLU | CYS | HIS | ILE | LYS | 5 |
|---|---|---|---|---|---|---|---|---|---|---|---|---|---|---|---|
| ASP | GLU | LEU | ASP | LYS | MET | THR | GLY | THR | ASP | LEU | MET | ILE | SER | ILE | 20 |
| ASN | GLU | PRO | ASN | PHE | PHE | ARG | LYS | HIS | VAL | SER | ASN | CYS | PRO | ASN | 35 |
| GLU | ALA | ALA | PHE | LEU | ASN | ARG | ALA | ALA | ARG | CYS | ASP | ASP | THR | LYS | 50 |
| LEU | LYS | MET | ASN | ILE | SER | GLU | GLU | PHE | ASN | LYS | LEU | LYS | GLN | PHE | 65 |
| VAL | SER | GLN | GLY | THR | GLN | THR | LEU | VAL | ASN | VAL | HIS | LEU | LEU | THR | 80 |
| GLU | LYS | ASN | VAL | LYS | GLU | GLN | LYS | LYS | ASN | CYS | THR | SER | LYS | GLU | 95 |
| LYS | ARG | LEU | LEU | ARG | GLU | ILE | LYS | THR | CYS | ASP | ALA | CYS | PHE | LEU | 110 |
| LYS | GLY | SER | ILE |  |  |  | THR | CYS | TRP | ASN | LYS | ILE | LEU | LEU | 125 |
|  |  |  |  |  |  |  |  |  |  |  |  |  |  |  | 129 |

Various biologically active derivatives or analogs of the foregoing polypeptides could also be used for the present inventive methods and compositions. As used herein, conspecific IL-7 or derivatives thereof, refer to polypeptides having substantial amino acid sequence homology to the native IL-7 polypeptide of that specific mammalian species and substantially equivalent biological activity. For example, a conspecific human IL-7 polypeptide or a polypeptide derivative will have an amino acid sequence substantially similar to the human native IL-7 polypeptide such that it should not be recognized as foreign by the recipient's immune system. Substantially equivalent biological activity means similar results in in standard bioassays or assays measuring IL-7 receptor binding affinity. IL-7 derivatives further encompass various non-polypeptide compound that display IL-7 biological activity. These compounds include IL-7 receptor agonists. The IL-7 receptor has been described in Goodwin et al. *Cell* 60:941 1990.

IL-7 polypeptides are preferably produced by recombinant DNA techniques. A recombinant DNA expression system inserts a clone encoding a conspecific IL-7 polypeptide or a polypeptide derivative thereof with IL-7 biological activity into an expression vector. The expression vector is inserted into a host cell. The host cell's protein synthesis machinery synthesizes the recombinant IL-7 polypeptide.

Recombinant expression vectors include synthetic or cDNA-derived DNA fragments encoding IL-7 polypeptides or biologically active derivatives thereof. The DNA encoding an IL-7 polypeptide or derivative thereof is operably linked to a suitable transcriptional or translational regulatory or structural nucleotide sequence, such as one derived from mammalian, microbial, viral or insect genes. Examples of regulatory sequences include, for example, a genetic sequence having a regulatory role in gene expression (e.g., transcriptional promoters or enhancers), an optional operator sequence to control transcription, a sequence encoding suitable mRNA ribosomal binding sites, and appropriate sequences which control transcription and translation initiation and termination. Nucleotide sequences are operably linked when the regulatory sequence functionally relates to the structural gene. For example, a DNA sequence for a signal peptide (secretory leader) may be operably linked to a structural gene DNA sequence for an IL-7 polypeptide or derivative thereof if the signal peptide is expressed as a precursor amino acid sequence which participates in the secretion of the IL-7 polypeptide. Further, a promoter nucleotide sequence is operably linked to a coding sequence (e.g., structural gene DNA) if the promoter nucleotide sequence controls the transcription of the structural gene nucleotide sequence. Still further, a ribosome binding site may be operably linked to a structural gene nucleotide coding sequence (e.g., IL-7 polypeptide) if the ribosome binding site is positioned within the vector to encourage translation.

Suitable host cells for expression of conspecific IL-7 polypeptides or derivatives thereof include prokaryotes, yeast or higher eukaryotic cells under the control of appropriate promoters. Prokaryotes include gram negative or gram positive organisms, for example *E. coli* or bacilli. Suitable prokaryotic hosts cells for transformation include, for example, *E. coli, Bacillus subtilis, Salmonella typhimurium,* and various other species within the genera Pseudomonas, Streptomyces, and Staphylococcus. Higher eukaryotic cells include established cell lines of mammalian origin as described below. Cell-free translation systems could also be employed to produce mammalian conspecific IL-7 polypeptides or derivatives thereof using RNAs derived from the DNA constructs disclosed herein. Appropriate cloning and expression vectors for use with bacterial, fungal, yeast, and mammalian cellular hosts are described, for example, in Pouwels et al. *Cloning Vectors: A Laboratory Manual*, Elsevier, N.Y., 1985.

When an IL-7 polypeptide or derivative thereof is expressed in a yeast host cell, the nucleotide sequence (e.g., structural gene) that codes on expression for an IL-7 polypeptide or derivative thereof may include a leader sequence. The leader sequence enables improved extracellular secretion of translated polypeptide by a yeast host cell.

Alternatively, in a prokaryotic host cell, such as *E. coli*, the IL-7 polypeptide or derivative thereof may include an N-terminal methionine residue to facilitate expression of the recombinant polypeptide in a prokaryotic host cell. The N-terminal Met may be cleaved from the expressed recombinant IL-7 polypeptide or derivative thereof. Moreover, prokaryotic host cells may be used for expression of IL-7 polypeptides or derivatives thereof that do not require extensive proteolytic and disulfide processing.

The recombinant expression vectors carrying the recombinant IL-7 structural gene nucleotide sequence or derivative thereof are transfected or transformed into a substantially homogeneous culture of a suitable host microorganism or mammalian cell line. Examples of suitable host cells include bacteria such as *E. coli*, yeast such as *S. cerevisiae*, or a mammalian cell line such as Chinese Hamster Ovary (CHO) cells.

Transformed host cells are cells which have been transformed or transfected with IL-7 or a derivative thereof structural gene nucleotide sequences. Expressed IL-7 polypeptides will be located within the host cell and/or secreted into culture supernatant, depending upon the nature of the host cell and the gene construct inserted into the host cell.

Expression vectors transfected into prokaryotic host cells generally comprise one or more phenotypic selectable markers. A phenotypic selectable marker is, for example, a gene encoding proteins that confer antibiotic resistance or that supply an autotrophic requirement, and an origin of replication recognized by the host to ensure amplification within the host. Other useful expression vectors for prokaryotic host cells include a selectable marker of bacterial origin derived from commercially available plasmids. This selectable marker can comprise genetic elements of the cloning vector pBR322 (ATCC 37017). pBR322 contains genes for ampicillin and tetracycline resistance and thus provides simple means for identifying transformed cells. The pBR322 "backbone" sections are combined with an appropriate promoter and an IL-7 structural gene sequence. Other commercially vectors include, for example, pKK223-3 (Pharmacia Fine Chemicals, Uppsala, Sweden) and pGEM1 (Promega Biotec, Madison, Wis., USA).

Promoter sequences are commonly used for recombinant prokaryotic host cell expression vectors. Common promoter sequences include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9 (ATCC 37092)) and pPlc28 (resident in *E. coli* RR1 (ATCC 53082)).

Conspecific mammalian IL-7 polypeptides and derivative polypeptides may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid, an autonomously replicating sequence (ARS), a promoter region, sequences for polyadenylation, and sequences for transcription termination. Preferably, yeast vectors include an origin of replication sequence and selectable marker. Suitable promoter sequences for yeast vectors include promoters for metallothionein, 3-phosphoglycerate kinase (Hintzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EP-A-73,657.

Yeast vectors can be assembled, for example, using DNA sequences from pBR322 for selection and replication in *E. coli* (Amp$^r$ gene and origin of replication). Other yeast DNA sequences that can be included in a yeast expression construct include a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader sequence directs secretion of heterologous polypeptides. The α-factor leader sequence is often inserted between the promoter sequence and the structural gene sequence. See, e.g., Kurjan et al., *Cell* 30:933, 1982; and Bitter et al., *Proc. Natl. Acad. Sci. U.S.A.* 81:5330, 1984. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. U.S.A.* 75:1929, 1978. The Hinnen et al. protocol selects for Trp+ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant IL-7 polypeptide or derivatives thereof. Examples of suitable mammalian host cell lines include the COS-7 lines of monkey kidney cells (Gluzman *Cell* 23:175, 1981), L cells, C127 cells, 3T3 cells, Chinese hamster ovary (CHO) cells, HeLa cells, and BHK cell lines. Suitable mammalian expression vectors include nontranscribed elements such as an origin of replication, a promoter sequence, an enhancer linked to the structural gene, other 5' or 3' flanking nontranscribed sequences, such as ribosome binding sites, a polyadenylation site, splice donor and acceptor sites, and transcriptional termination sequences.

Transcriptional and translational control sequences in mammalian host cell expression vectors may be provided by viral sources. For example, commonly used mammalian cell promoter sequences and enhancer sequences are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Further, conspecific mammalian genomic IL-7 promoter, control and/or signal sequences may be utilized, provided such control sequences are compatible with the host cell chosen. Exemplary vectors can be constructed as disclosed by Okayama and Berg (*Mol. Cell. Biol.* 3:280, 1983).

IL-2 polypeptides and polypeptide derivatives thereof and IL-4 polypeptides and polypeptide derivatives thereof can be made in much the same way as is described herein for IL-7 polypeptides. Moreover, IL-2 derivatives include non-polypeptide compounds that can act as IL-2 receptor agonists. The IL-2 receptor has been described in, for example, U.S. patent application Ser. No. 626,667, filed Jul. 2, 1984, the disclosure of which is incorporated by reference herein, and in European Patent Application EP-A-0162699, published on Sep. 23, 1988.

Mammalian DLN or CLN cells do not survive in vitro in cell culture beyond 7 to 10 days under normal culture conditions. Addition of an IL-7 polypeptide or a derivative thereof into the culture medium enables long term cell survival and growth well beyond 10 days under the same or similar culture conditions. Moreover, further addition of a conspecific IL-2 polypeptide or a derivative thereof or an IL-4 polypeptide or a derivative thereof does not mitigate the cell survival lengthening effects of IL-7. Addition of mouse IL-2 to cultures of mouse DLN's extended the long term survival of the cells but the cells appeared to be unhealthy and visually clumped when examined under microscopic conditions. Moreover DLN cells incubated ex vivo with only IL-2 for extended periods of time did not exhibit significant CTL or LAK activity, in contrast to DLN cells kept in long term culture with at least IL-7 as an added cytokine. Further addition of a population of mitotically inactivated tumor cells also does not adversely effect DLN cell survival in culture in the presence of an IL-7 polypeptide. In fact, DLNs in cell culture are often cytolytic for added tumor cells displaying the specific antigen and we have found that the addition of mitotically inactivated specific tumor cells enhances DLN cell survival in culture by inducing proliferation of the cultured DLN cells.

Proliferated mammalian cytolytic T lymphocytes have lytic specificity for cells (e.g., tumor cells) displaying a specific antigen. Cytolytic T cells are obtained from draining lymph nodes or other sources (e.g., peripheral blood or spleen) that have been previously exposed to the specific antigen. After ex vivo exposure to a culture medium comprising an IL-7 polypeptide or a derivative thereof, the cytolytic T cells become activated and retain their lytic specificity for target cells displaying the specific antigen. The lytic activity of the activated and proliferated CTL cells incubated in the presence of IL-7 or a derivative thereof in the culture medium is significantly greater than the same cells incubated with an IL-2 polypeptide in the culture medium. CLN cells incubated in the presence of IL-7 display CD8+ LAK activity. However, specific antigen-directed T cells are preferred. Long term cultures of such cells incubated in the presence of an IL-7 polypeptide display minimal LAK (lymphokine activated killer) activity and predominantly CTL activity specific for target cells (e.g., tumor cells, virally infected cells or viruses) displaying the specific antigen. LAK activity, mediated by NK cells as well as CD8 positive lymphocytes, is characteristic of IL-2 activation, and is the predominant activity of IL-2 activated lymphocytes. IL-7 activated cytolytic T cells of the present invention have predominantly CTL activity characterized by antigen specificity for target cells, such as tumor cells. CTL activity is enhanced by further addition of an IL-2 polypeptide or derivatives thereof and/or an IL-4 polypeptide or derivatives thereof to the culture medium. However, in vivo therapeutic efficacy is minimally enhanced (e.g., 2×) by further addition of IL-2 and/or IL-4. Moreover, further addition of mitotically inactivated specific tumor cells provides a source of specific antigen to help to proliferate the cytolytic T lymphocytes in culture. This can further enhance CTL activity of DLN cells in culture.

Syngeneic peripheral lymphoid cells (e.g., DLN cells) are obtained from an individual after the lymphoid cells have had an opportunity to be exposed to the specific antigen. Such cells can be obtained, for example, from a draining lymph node, such as a lymph node draining a tumor or a virally infected site. Peripheral lymphoid cells may be obtained, for example, by aspiration or by removal of the draining lymph node, followed by dissection. Lymphoid cells from a draining lymph node may be placed into a single cell suspension of lymphoid cells by mechanical means, such as a screen. The cells may be sorted in a cell sorter to remove unwanted fibroblasts and then placed into a culture medium comprising an IL-7 polypeptide or a derivative thereof.

Cells obtained from a draining lymph node generally contain a population of T cells that had been previously exposed to the specific antigen. Standard culture medium (e.g., RPMI 1640, 1 mM sodium pyruvate, 2 mM glutamine, 0.1 mM non-essential amino acids, 50 U/ml penicillin, 50 U/ml streptomycin, 10% fetal calf serum, and $5 \times 10^{-5}$ M 2-mercaptoethanol) is added to the cells. Another example of standard culture media is minimal essential medium. The culture conditions are those optimal for cell survival and proliferation, such as in a humidified incubator, at 6% $CO_2$ in air atmosphere at approximately 37° C.

An IL-7 polypeptide or a derivative thereof with IL-7 biological activity is added to the culture medium. The amount of IL-7 polypeptide added is sufficient to induce CTL activity in the cultured lymphoid cells. Preferably, the amount of human IL-7 administered in the culture medium is from about 2.5 ng/ml to about 20 ng/ml. Most preferably, the amount of an IL-7 polypeptide administered is about 10 ng/ml. Other compounds can be added to the culture medium to enhance cell survival in culture and the augment CTL activity activation. The amount of IL-7 derivatives added to the culture medium is dependent upon the specific activity of the derivative. For example, a derivative approximately equally potent to wild type human IL-7 will be added at the same concentration on a weight basis. The other compounds include a conspecific IL-2 polypeptide or derivative thereof and/or a conspecific IL-4 polypeptide or a derivative thereof, and/or a population of mitotically inactivated tumor cells bearing the specific antigen. Preferred culture concentrations of added cytokine are from about 0.5 to about 20 ng/ml for IL-2, and from about 1 to about 20 ng/ml of IL-4.

A conspecific IL-2 polypeptide or derivative thereof is any polypeptide or other organic molecule that displays IL-2 biological activity. IL-2 biological activity is characterized by an ability to bind to a species specific IL-2 receptor polypeptide. IL-2 biological activity can also be measured by stimulation of CTLL or HT2 cell proliferation in vitro. Both CTLL and HT2 cell lines are dependent upon the presence of IL-2 activity in the medium for survival.

The population of mitotically inactivated tumor cells bear the same specific antigen as was previously exposed to the lymphocytes. Mitotic inactivation means that the tumor cells may be "alive" (i.e., capable of cellular metabolism and respiration) but are substantially incapable of cellular division and colony growth. Thus, mitotically inactivated tumor cells provide a source of specific antigen to the culture medium without the ability to overwhelm and overgrow the cytolytic T lymphocytes and other cell types in culture.

Figure 19A:
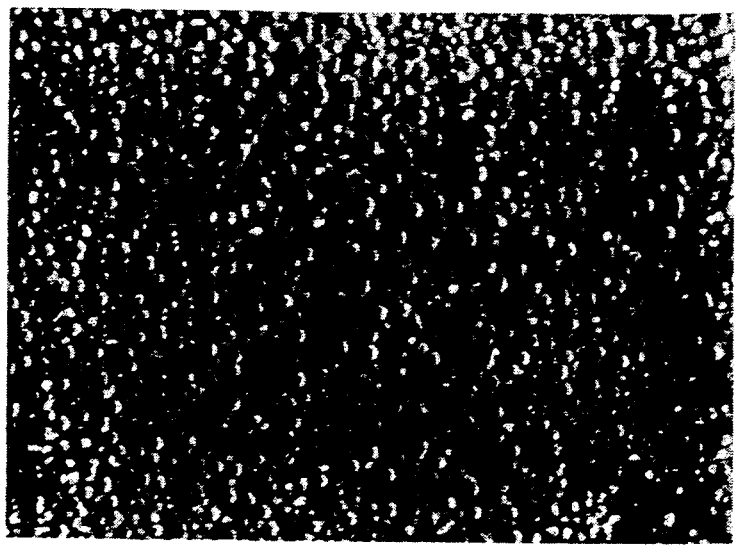
FIG. 19A depicts DLN cells grown with mouse IL-7.
Figure 19B:
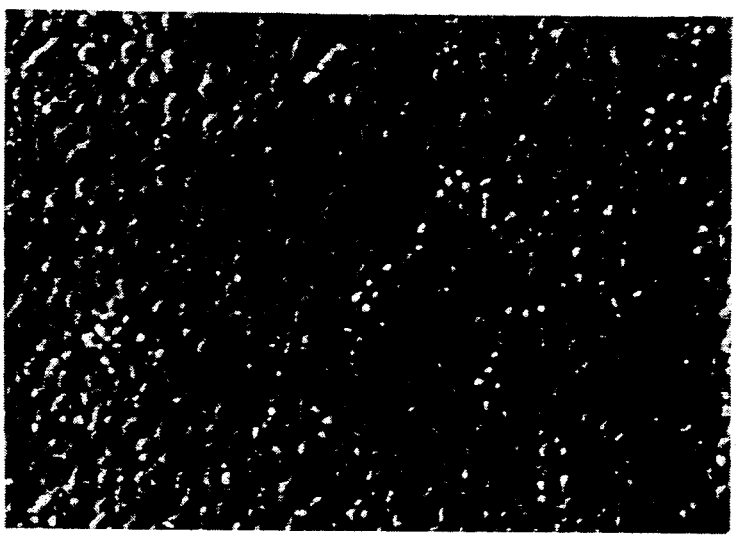
FIG. 19B shows the cells grown with mouse IL-7 and mouse IL-2.
Figure 19C:
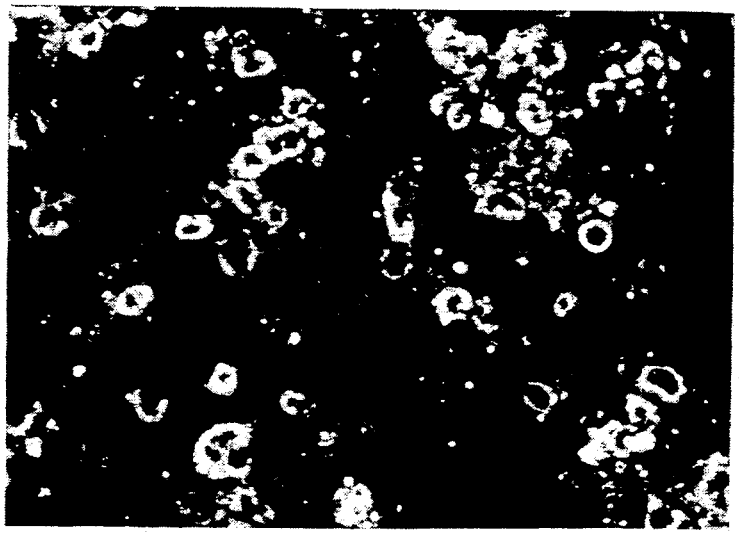
FIG. 19C shows the cells grown with only IL-2. Cells in culture without added cytokine would not survive to the nine week point shown in the three photographs.

The inventive cells, grown under culture conditions described herein, are capable of survival for a significantly longer period of time with an IL-7 polypeptide or a derivative thereof present in the culture medium than in the absence of added IL-7 biological activity. Cultured lymph node cells or T lymphocytes are capable of in vitro survival under culture conditions for at most 7 to 10 days under optimal culture conditions in the absence of added IL-7 biological activity. The same cells, by contrast, are capable of at least eighteen weeks of continuous culture in the presence of IL-7 biological activity. The photographs reprinted in FIG. 19 show photomicrographs of nine week old cultures of mouse DLNs that have been cultured in the presence of mouse IL-2, mouse IL-7 or a combination of mouse IL-2 and mouse IL-7. Only cells cultured in the presence of IL-7 (with or without IL-2) remained active, displayed more pseudopods to adhere to the culture well base and retained more specific (i.e., antigen specific) cytolytic activity. Cells cultured without addition of either IL-2 or IL-7 did not survive and could not be investigated.

A population of cells obtained from a draining lymph node and cultured ex vivo exhibit CTL activity, were characterized by CD8 positive T cells directed to cells bearing the specific antigen, and by a relative lack of non-specific LAK activity (mediated by non-specific lytic activity) characterized by NK cells. CTL activity is thought to be mediated by antigen-specific cytolytic T cells that display lytic activity directed only to those cells displaying the specific antigen. CTL activity is a more desirable form of lytic activity than LAK activity because it is target cell or antigen specific. Thus immune therapy with cells having CTL activity will have fewer side effects than comparable lytic activity with cells having non-specific LAK activity.

Activated cultured T lymphoid cells, cultured in the presence of a biologically effective amount of an IL-7 polypeptide or biologically active derivative thereof, are administered to the individual in a form of adoptive immunotherapy. The particular cytokine or cytokines used to activate CTL activity ex vivo in the cells (e.g., IL-7 and possibly IL-4 and/or IL-2) can be co-administered along with the cells. Preferred daily dosages for administration of cytokines include from about 10 to about 2000 μg/kg/day for IL-2, from about 4 to about 1000 μg/kg/day for IL-4 and IL-7. Most preferably, the daily dose of IL-2 is administered each day in three separate doses and IL-4 and IL-7 are administered twice daily (bid).

The lymphoid cells require activation in culture in the presence of an IL-7 polypeptide or derivative thereof for at least 4 days. The activated population of cells are administered by intravenous infusion into the individual, or by injection directly to a tumor site. The activated population of cells may be administered by other acceptable means of administration as well.

Cells displaying the specific antigen are the target of CTL activity. The specific antigen may be, for example, a tumor antigen displayed by a specific population of tumor cells or a viral antigen displayed by a population of host cells that are infected by a virus. Example of known tumor antigens include Meth A, tumor $A_5$, and P815 tumor $A_5$, and known viral antigens include Flu, Vaccinia, and Lymphochoriomeningitis virus. Cells displaying the specific antigen become target cell for CTL activity of the activated lymphoid cells.

The following examples are designed to illustrate various aspects of the present invention.

EXAMPLE 1

This example illustrates the effects of inclusion of an IL-7 polypeptide into an in vitro culture medium of DLNs. The administration of IL-7 into the culture medium enhances anti-tumor CTL activity in vitro and anti-tumor therapeutic efficacy in vivo. C3H mice were injected with $3 \times 10^6$ 1024 tumor cells. Ten days later draining lymph nodes (DNL) were surgically removed under sterile conditions, dissociated into a single cell suspension, and placed into tissue culture. Recombinant human IL-7, as described in U.S. Pat. No. 4,965,195, filed Oct. 7, 1988 the disclosure of which is incorporated by reference herein, was added to the culture medium at 0 (control), 2.5, 10, and 20 ng/ml concentrations. Parallel cultures of control lymph nodes (CLN) cells obtained from C3H mice not previously exposed to the 1024 tumor were placed in the same culture medium.

After four days in culture, culture aliquots were assayed for in vitro cytolytic activity. Cytolytic activity was determined by a six hour $^{51}$Cr-release assay as described in Lynch et al. J. Immunol. 136:1521 1986. CLN cells cultured without IL-7 did not display anti-tumor cytolytic activity. CLN cells cultured with 20 ng/ml IL-7 displayed only "modest" cytolytic activity that is consistent with residual murine LAK activity induced by IL-7. DLN cells cultured in medium alone exhibited anti-tumor cytolytic activity without IL-7 added to culture medium. However, cytolytic activity was significantly enhanced by the addition of IL-7 to the culture medium. Cytolytic data are presented in FIG. 1. FIG. 1 compares cytolytic activity (i.e., percent lysis) at several effector cell to target cell ratios for CLNs cultured without IL-7, CLNs cultured with 20 ng/ml IL-7, DLNs cultured without IL-7, and DLNs cultured with different concentrations of IL-7. DLNs cultured with IL-7 displayed the most lytic activity at all effector to target ratios.

In vivo efficacy of the cultured cells was determined by adoptively transferring (by intravenous injection) graded numbers of DLN cells ($1 \times 10^6$, $3 \times 10^6$, or $6 \times 10^6$ cells), that were cultured with or without IL-7, to groups of C3H mice (four mice per group). The mice were previously irradiated with a sublethal (500 rads) dose to inhibit generation of an endogenous primary immune response. Control mice (irradiated with 500 rads) either received no cells or $6 \times 10^6$ CLN cells cultured for four days in culture medium with or without 20 ng/ml of IL-7. Mice in all treatment groups were challenged by intradermal injection of $5 \times 10^5$ viable 1024 tumor cells. Tumor growth rates were determined over the following 36 day period by measuring the tumor size (mm$^2$).

Figure 2:
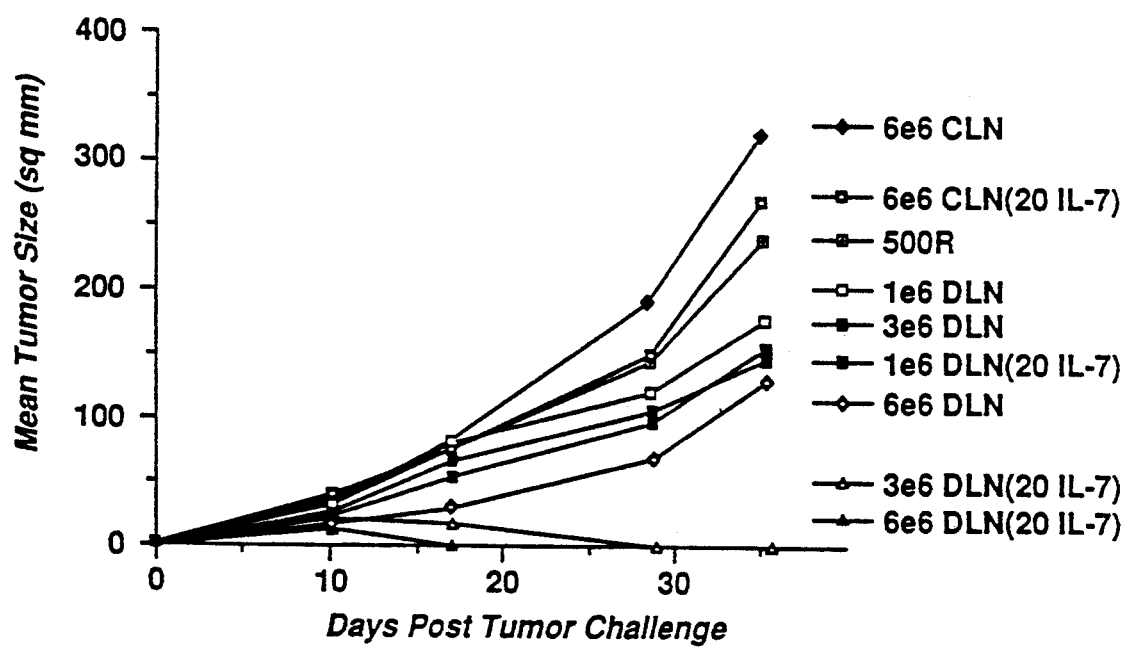
FIG. 2 compares tumor growth rates in vivo of mice challenged with tumor cells and treated with various members of CLNs and DLNs cultured in 20 ng/ml of recombinant murine IL-7 as compared with CLNs and DLN cultured in medium alone. The best anti-tumor therapeutic activity was shown by DLNs incubated with IL-7. Complete tumor regression occurred in mice that received either $3 \times 10^6$ or $6 \times 10^6$ DLN cells previously incubated with 20 ng/ml of murine IL-7.

The tumor challenge grew at similar rates in irradiated mice that received no cells, $6 \times 10^6$ CLN cells, or $6 \times 10^6$ CLN cells cultured with 20 ng/ml IL-7 (FIG. 2). Tumor growth rates were significantly slower in mice that received either $1 \times 10^6$, $3 \times 10^6$ or $6 \times 10^6$ DLN cells cultured in the absence of IL-7 but no tumor cells were detected (FIG. 2). Mice that received either $3 \times 10^6$ or $6 \times 10^6$ DLN cells cultured in 20 ng/ml IL-7 were found to reject the tumor challenge in all instances. Mice that received $1 \times 10^6$ DLN cells cultured in 20 ng/ml IL-7 grew the tumor challenge at a rate similar to mice who received $6 \times 10^6$ DLN cells cultured in medium alone. These data indicate that DLN cells cultured with IL-7 were approximately six times more therapeutically effective in vivo than the same DLN cells cultured without IL-7.

Figure 3:
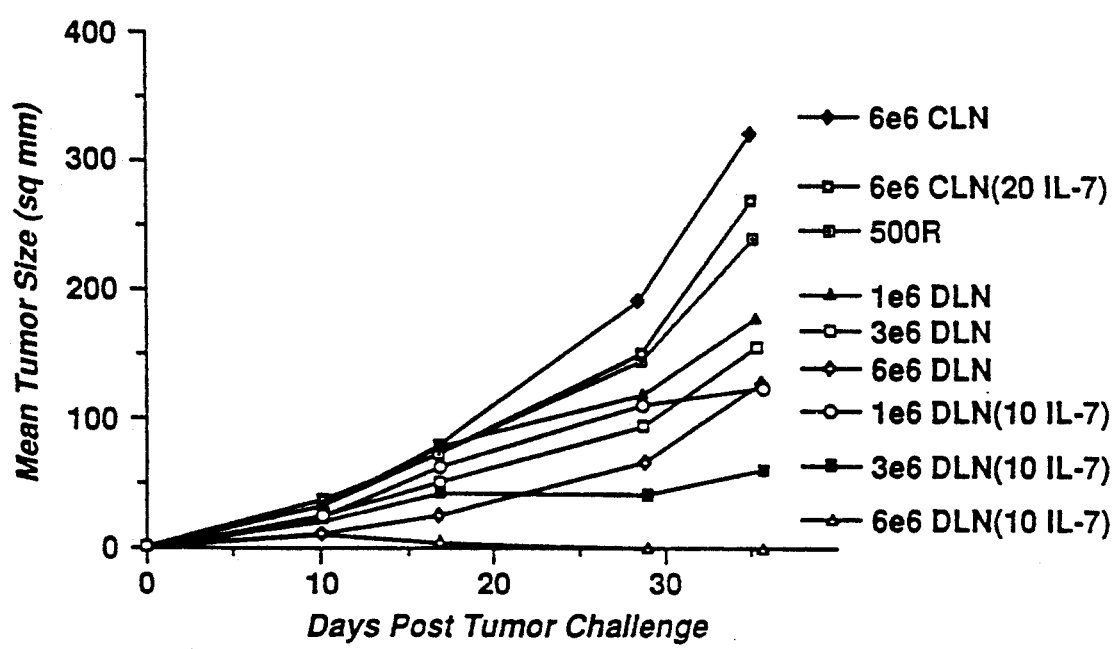
FIG. 3 illustrates a comparison of mean tumor size at several days after injection of tumor cells into C3H mice that were also treated with several concentrations of CLNs or DLNs cultured in 10 ng/ml IL-7 compared to CLNs and DLNs cultured in medium alone. These data illustrate the comparative tumoricidal properties of the stimulated cytotoxic T lymphocytes. Complete regression of tumor size only occurred when the mice were injected with $6 \times 10^6$ DLN cells previously incubated with 10 ng/ml of IL-7.
Figure 4:
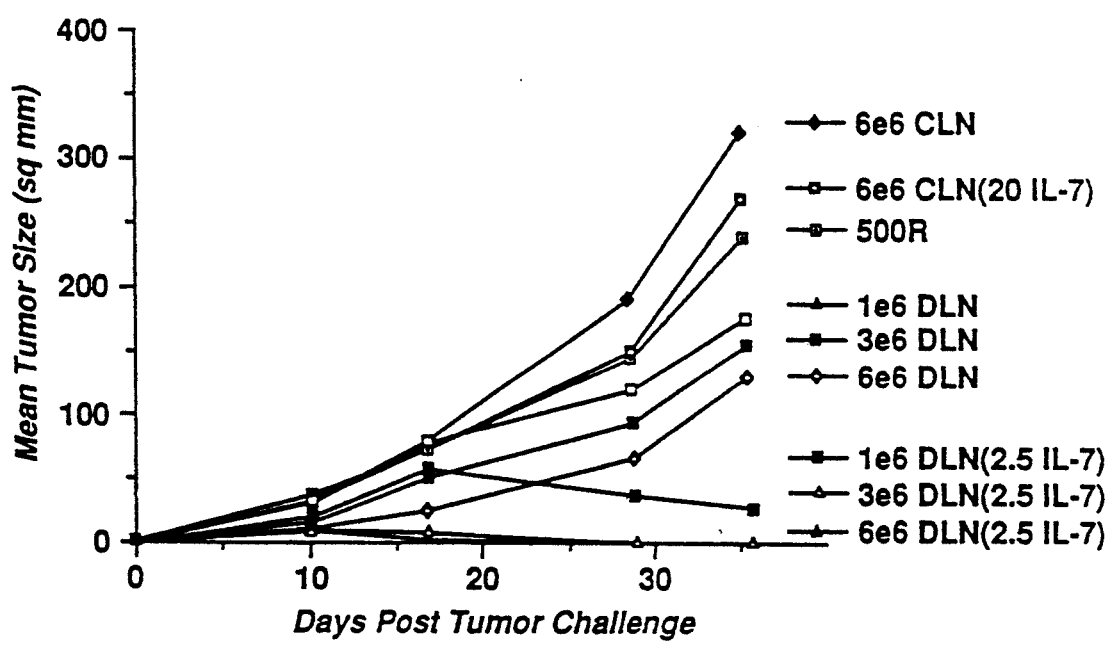
FIG. 4 depicts a comparison of mean tumor size in vivo at several days post tumor challenge using DLN cells cultured in medium containing 2.5 ng/ml of IL-7 compared with cells cultured in medium without IL-7. The best therapeutic effect was observed with DLNs incubated with IL-7.

FIGS. 3 and 4 show similar tumor growth rate observations when the culture medium contained 10 ng/ml and 2.5 ng/ml, respectively of IL-7. These data (in FIGS. 1-4) demonstrate the therapeutic efficacy of anti-tumor cytotoxic T lymphocyte (CTL) activity is enhanced approximately six-fold by ex vivo culturing of DLN cells in culture medium containing IL-7 as compared to cultures of DLN cells in medium alone. The in vivo anti-tumor effectiveness of the IL-7 cultured DLN cells cannot be attributed to IL-7 induced nonspecific LAK activity because mice receiving CLN cells cultured with 20 ng/ml of IL-7 grew the tumor challenge at a rate similar to control mice that received CLN cells cultured without IL-7.

EXAMPLE 2

This example illustrates the effects of inclusion of an IL-2 polypeptide to the culture medium together with an IL-7 polypeptide when cytolytic T cells are cultured ex vivo. DLNs and CLNs were obtained from C3H mice as described in Example 1. The DLN cells had been exposed eight days earlier to $2 \times 10^6$ viable 1024 tumor cells. DLN and CLN cells were dissociated into a single cell suspension and cultured in complete RPMI 1640 medium. The culture medium was supplemented with any one of (A) control medium without added cytokine, (B) 2 ng/ml IL-2, (C) 20 ng/ml IL-7, (D) 10 ng/ml IL-7, (E) 2 ng/ml IL-7, or (F) 2 ng/ml IL-2+10 ng/ml IL-7. After four days in culture, aliquots of cells from each culture were assayed for anti-tumor cytolytic activity in a six hour $^{51}$Cr-release assay as described in Example 1.

Figure 5:
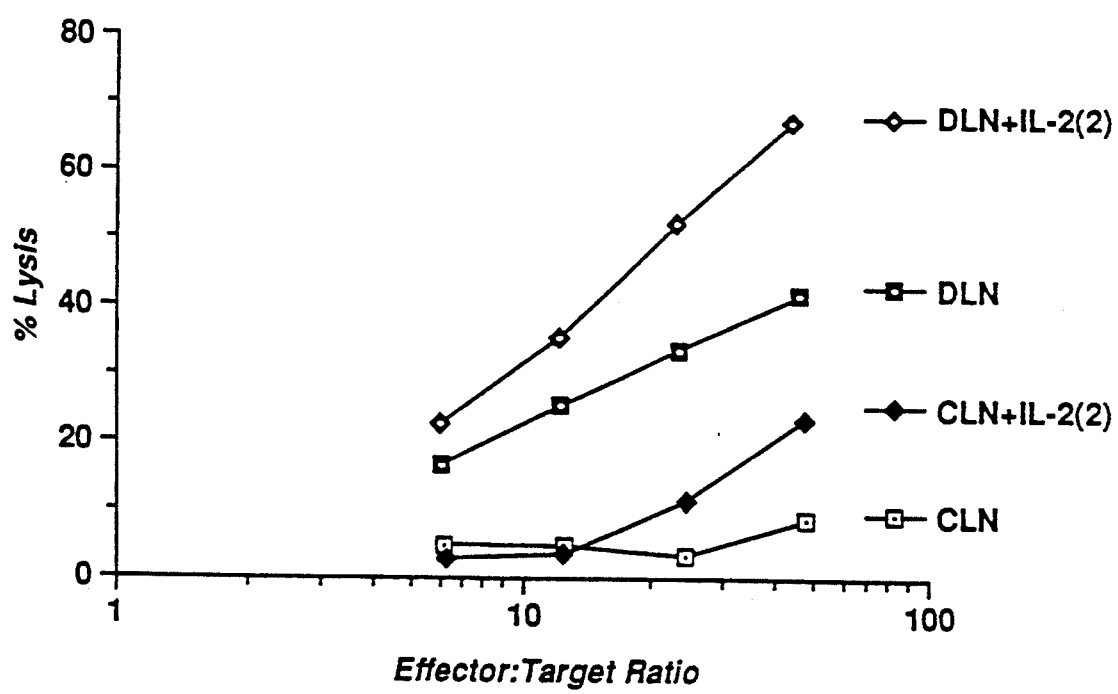
FIGS. 5–14 depict data from an experiment wherein draining lymph nodes (DLN) cells from C3H mice were were obtained from C3H mice that had been injected eight days previously with $2 \times 10^6$ viable 1024 tumor cells (each mouse). The DLN cells were cultured ex vivo in medium containing either IL-2, IL-7, or a combination of IL-2 and IL-7. Parallel cultures of control lymph nodes (CLN) obtained from C3H mice not exposed to tumor were set up and incubated ex vivo in medium alone or medium containing either IL-2 or a combination of IL-2 and IL-7. After four days in culture, the cell populations were assessed for in vitro anti-tumor cytolytic activity in a $^{51}Cr$-release assay and for in vivo anti-tumor activity by measuring tumor regression of a single mass. The data from this experiment are set forth in FIGS. 5–14.

FIG. 5 shows that no anti-tumor effector cell activity was detected with CLN cells cultured in medium without cytokine and a low level of LAK activity was detected with CLN cells cultured in medium containing 2 ng/ml of IL-2. Anti-tumor CTL activity was generated with DLN cells cultured in medium alone and this CTL activity was significantly enhanced when 2 ng/ml of IL-2 (B) was added to the culture medium (FIG. 5).

Figure 6:
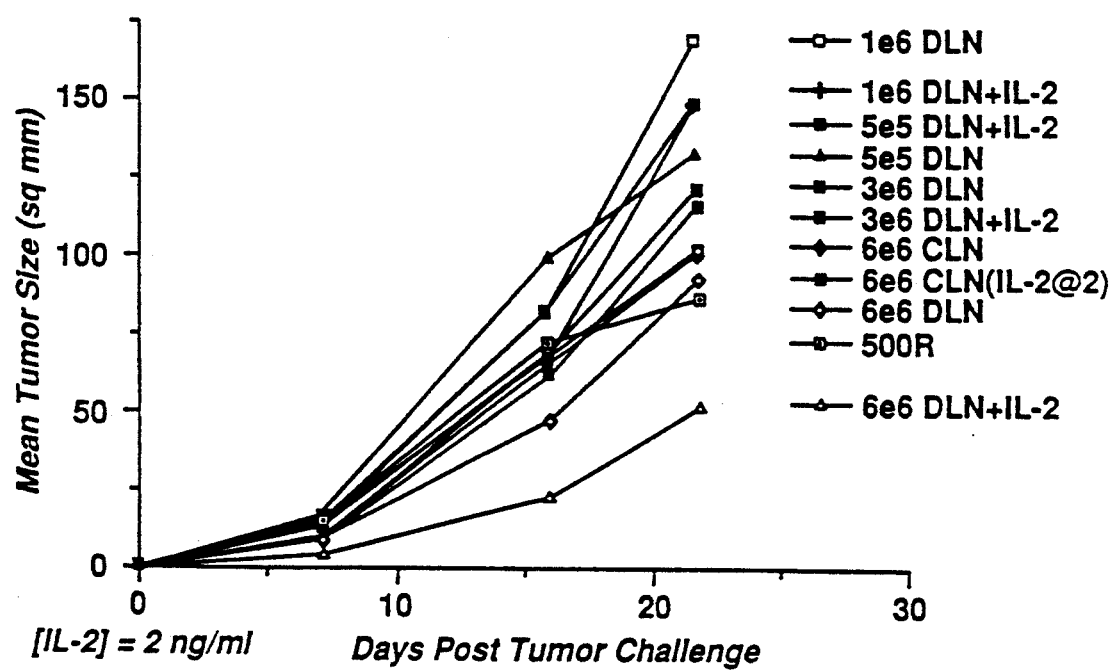

Therapeutic efficacy in vivo was measured by measuring 1024 tumor size in the same manner as in Example 1. FIG. 6 shows that mice that received CLN cells grown in culture without added cytokine and CLN cells grown with (B) 2 ng/ml IL-2, grew tumor challenge at rates similar to control irradiated mice that received no cells. FIG. 6 further illustrates that, in this experiment, the therapeutic efficacy of the cultured DLN cells was negligible because $6 \times 10^6$ DLN cells cultured without cytokine grew tumor at a similar rate to the control groups. Recipients of fewer numbers of control DLN cells grew tumor challenge at rates similar to or greater than that observed with control groups. DLN cells cultured with IL-2 (2 ng/ml) grew tumor challenge at a reduced rate from control groups (FIG. 6).

Figure 7:
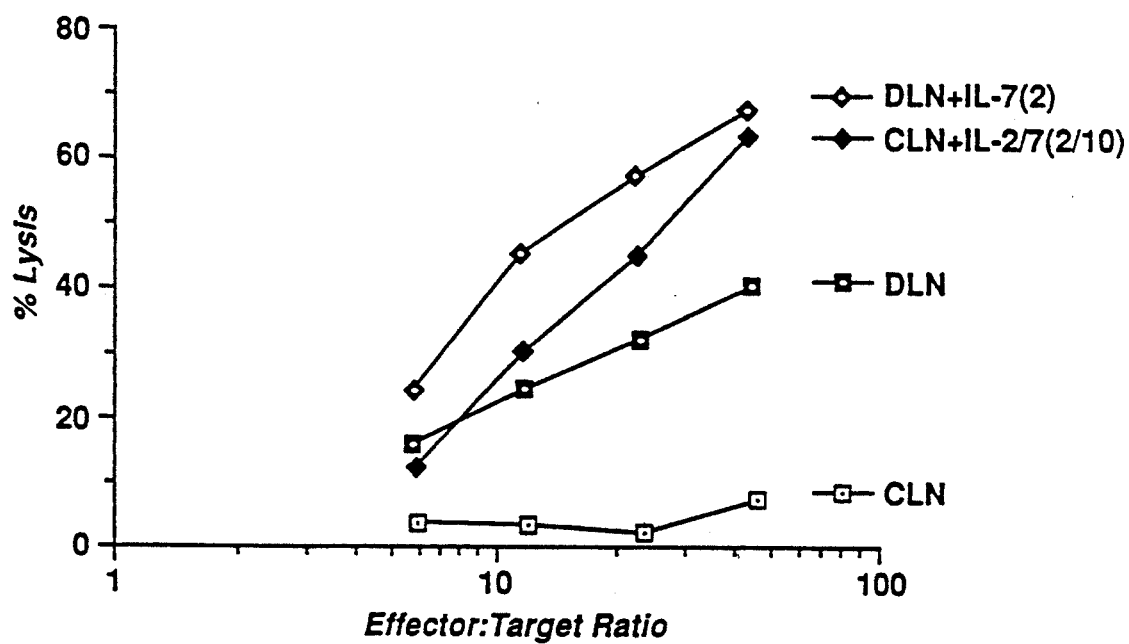
Figure 8:
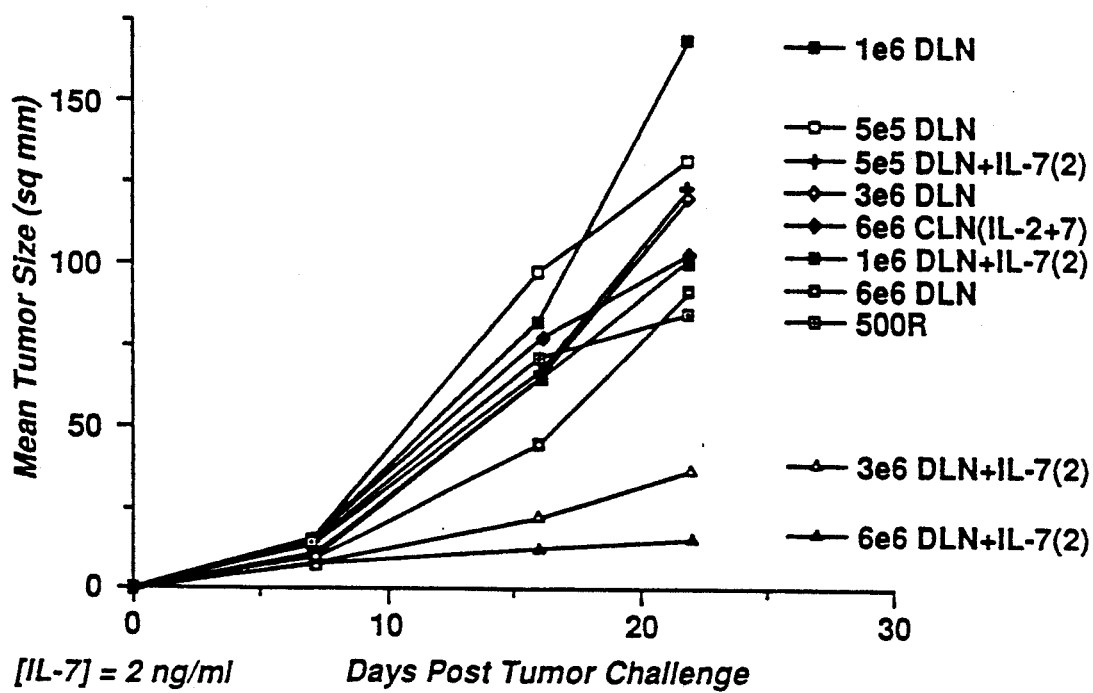
Figure 9:
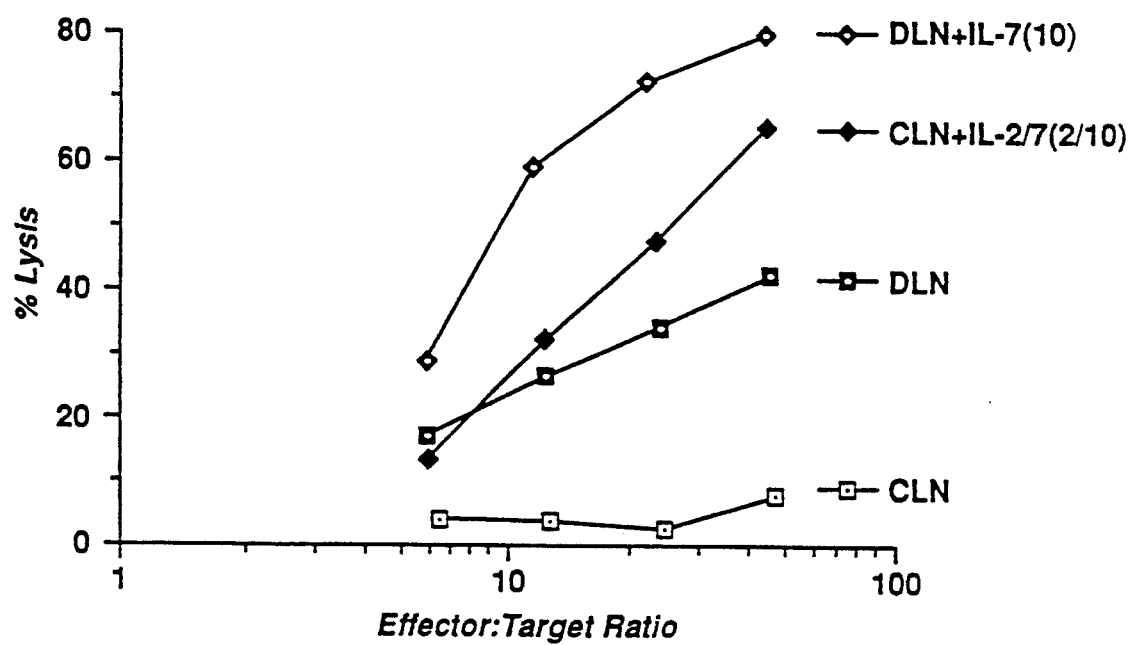
Figure 10:
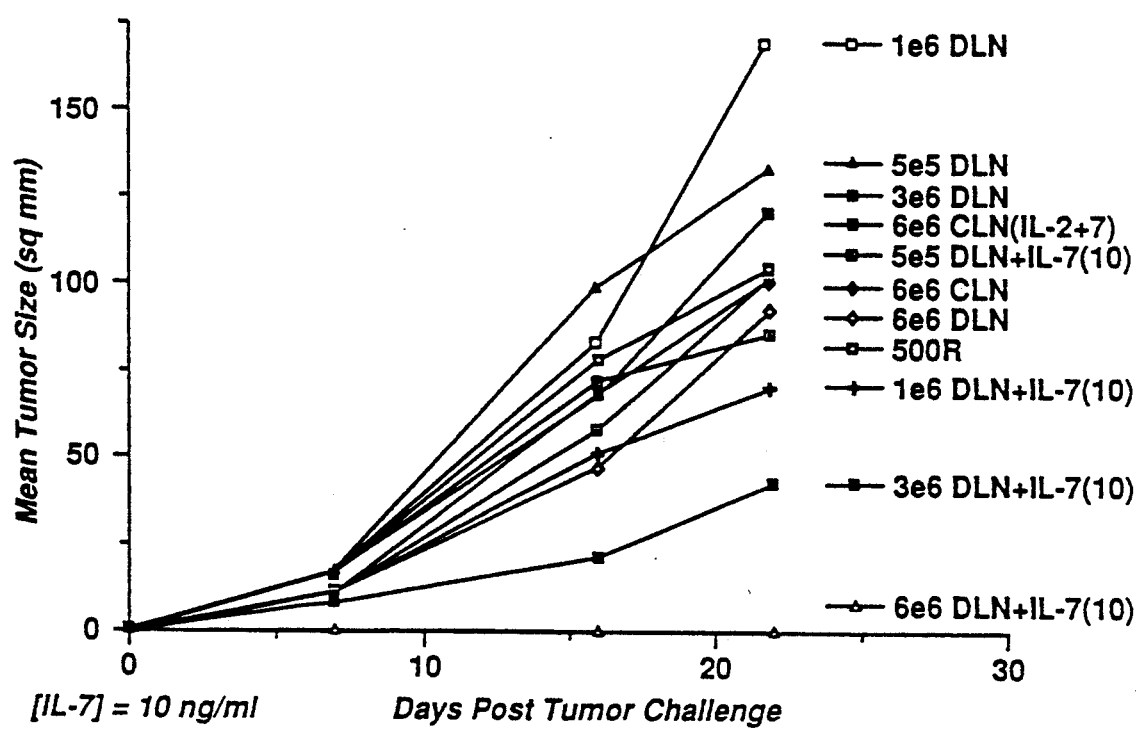
Figure 11:
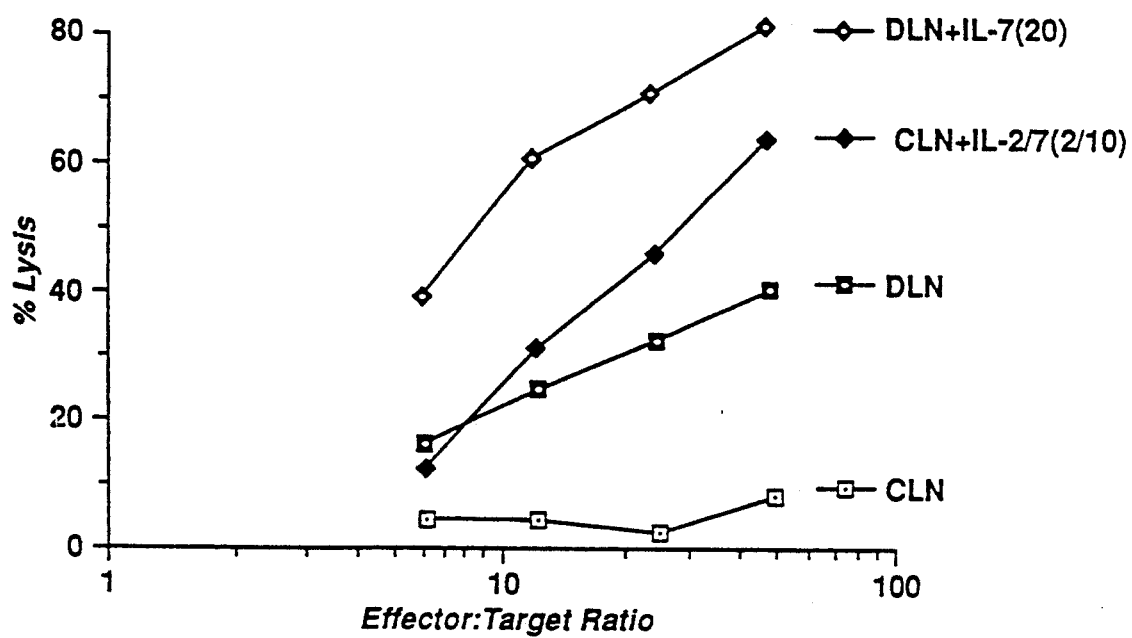
Figure 12:
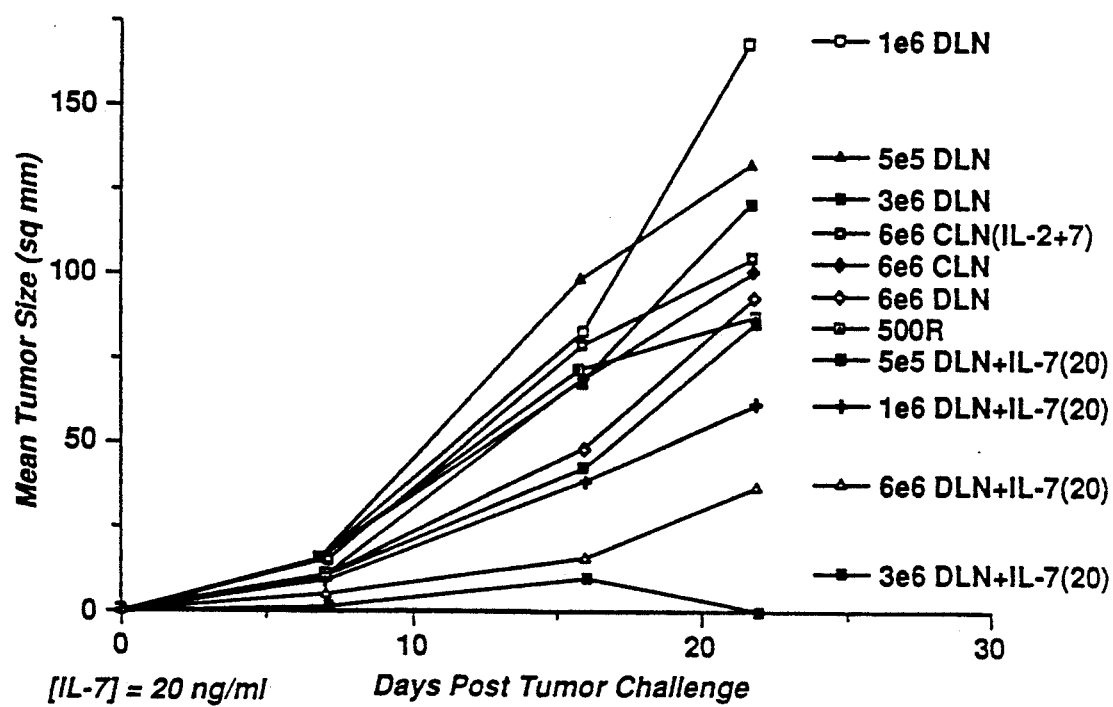
Figure 13:
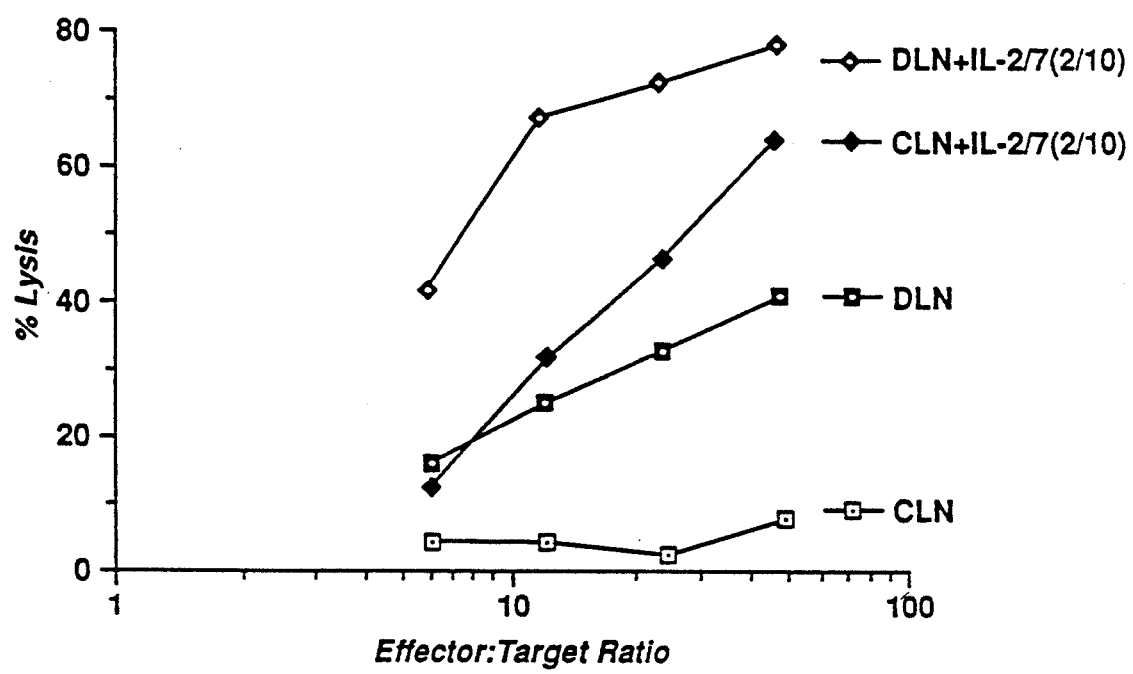
Figure 14:
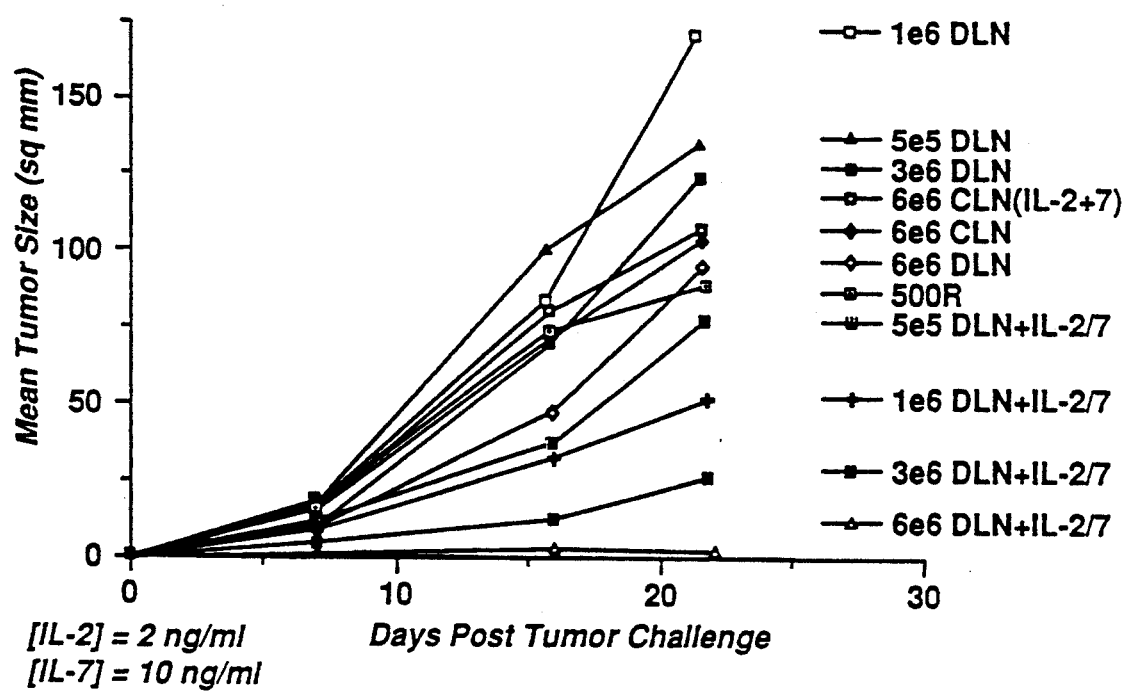

FIGS. 7, 9 and 11 show that DLN cells cultured in medium containing either 2, 10 or 20 ng/ml of IL-7, respectively had markedly enhanced anti-tumor cytolytic activity as compared to DLN cells cultured in medium alone. In vivo therapeutic efficacy of DLN cell populations (as determined by tumor growth rates in mice receiving titrated numbers of effector cells) was found to be enhanced approximately six-fold with DLN cells cultured with 2 ng/ml of IL-7 and 10 ng/ml of IL-7, and approximately 12-fold with DLN cells cultured with 20 ng/ml IL-7 (see FIGS. 8, 10 and 12). CLN cells cultured in 10 ng/ml IL-7 plus 2 ng/ml IL-2 did not mediate any detectable therapeutic effect in vivo, but demonstrated substantial tumoricidal LAK activity in vitro (FIG. 13). DLN cells cultured in 10 ng/ml IL-7 plus 2 ng/ml of IL-2 evidenced a 12-fold enhancement of therapeutic efficacy compared with DLN cells cultured in medium alone FIG. 14).

These data demonstrate that therapeutic efficacy of anti-tumor CTL activity generated during a four day ex vivo culture period from populations of DLN cells can be enhanced from about 6-fold to about 12-fold by culturing DLN cells in culture medium containing either IL-7 or a combination of predominantly IL-7 plus IL-2. However, DLN cells cultured in culture medium with IL-2 as the only added cytokine (i.e., without IL-7) were only marginally more therapeutically active in vivo. The increased therapeutic efficacy cannot be attributed to LAK activity because administration of CLN cells cultured in either 2 ng/ml of IL-2 or 10 ng/ml of IL-7 plus 2 ng/ml of IL-2 grew tumor challenge at rates similar to irradiated control mice that were not treated with cells or were treated with CLN cells cultured without cytokine.

EXAMPLE 3

This example illustrates anti-tumor CTL activity conferred by DLN and CLN cells maintained under long term culture conditions. B10 mice were injected with B10.5 tumor cells. DLN cells were obtained nine days later. Parallel CLN cells were obtained from B10 mice not exposed to B10.5 tumor cells. Lymphocyte cells were placed into a single cell suspension and cultured for four days in complete RPMI 1640 medium. After four days in culture conditions without added cytokine, the DLN cells were transferred to different culture conditions with added cytokine and/or mitotically inactivated tumor cells as indicated. DLN cell cultures incubated with mitotically-inactivated tumor cells but without added cytokine became overgrown with tumor cells. Conversely, DLN cell cultures incubated with both added IL-7 plus mitotically-inactivated tumor cells and possibly other cytokines remained DLN cell cultures. In vivo anti-tumor efficacy was determined by measuring tumor size in the same manner as Examples 1 and 2 using specific B10.5 tumor cells and non-cross-reactive B10.2 tumor cell lines.

Figure 15:
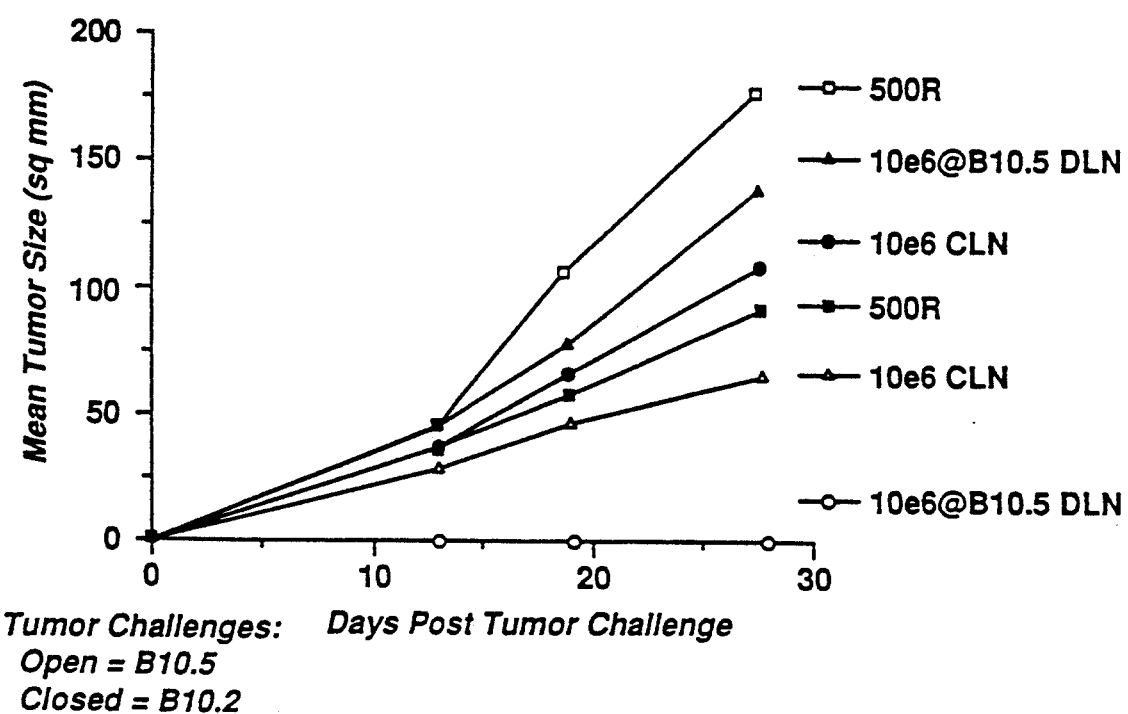

FIG. 15 shows that DLN cells rejected B10.5 tumor cells but not B10.2 tumor challenges. CLN cells, as expected, did not mediate rejection of either tumor cell line.

Long term DLN and CLN cultures were established with the cells obtained from the B10 mice. Irradiated (2000 rads) B10.5 specific tumor cells were added to each culture at a responder:stimulator ratio of 5:1. Culture medium either was not supplemented with cytokine or was supplemented with 5 ng/ml IL-2, 10 ng/ml IL-7, or 10 ng/ml IL-7 plus 2 ng/ml IL-2. Irradiated tumor cells were added to each of the DLN cultures. The amount of irradiation (2000 rads) is not enough to cause complete mitotic inhibition of the tumor cells. The DLN culture without added cytokine became completely overgrown with tumor cells. Other DLN cultures with some form of cytokine addition eliminated added tumor cells and continued to proliferate. DLN cultures were maintained with the same concentrations of cytokine but without subsequent in vitro stimulation with irradiated tumor cells.

Figure 16:
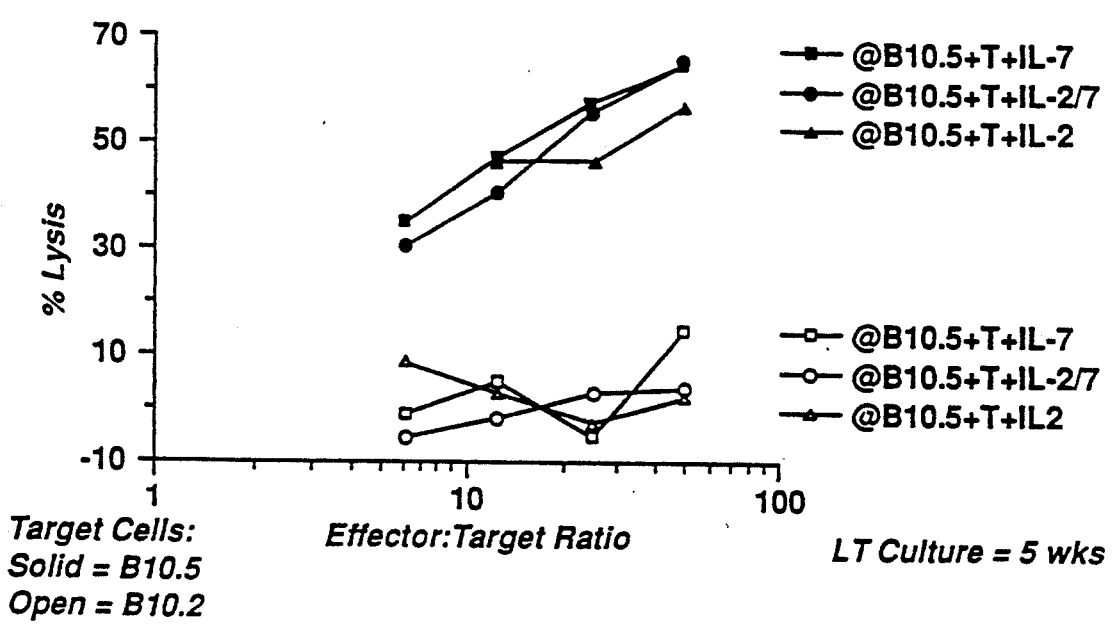

DLN cultures with added cytokine were continued for five weeks and then assayed for in vitro cytolytic activity. FIG. 16 shows that anti-tumor specific CTL activity was detected in all cases after five weeks in culture. Cytolytic activity was not detected when challenged with the B10.2 (non-specific) tumor cells. Flow cytometric analysis of these DLN cell populations (FIG. 17) revealed them to be predominantly CD8+·T cells.

Figure 18:
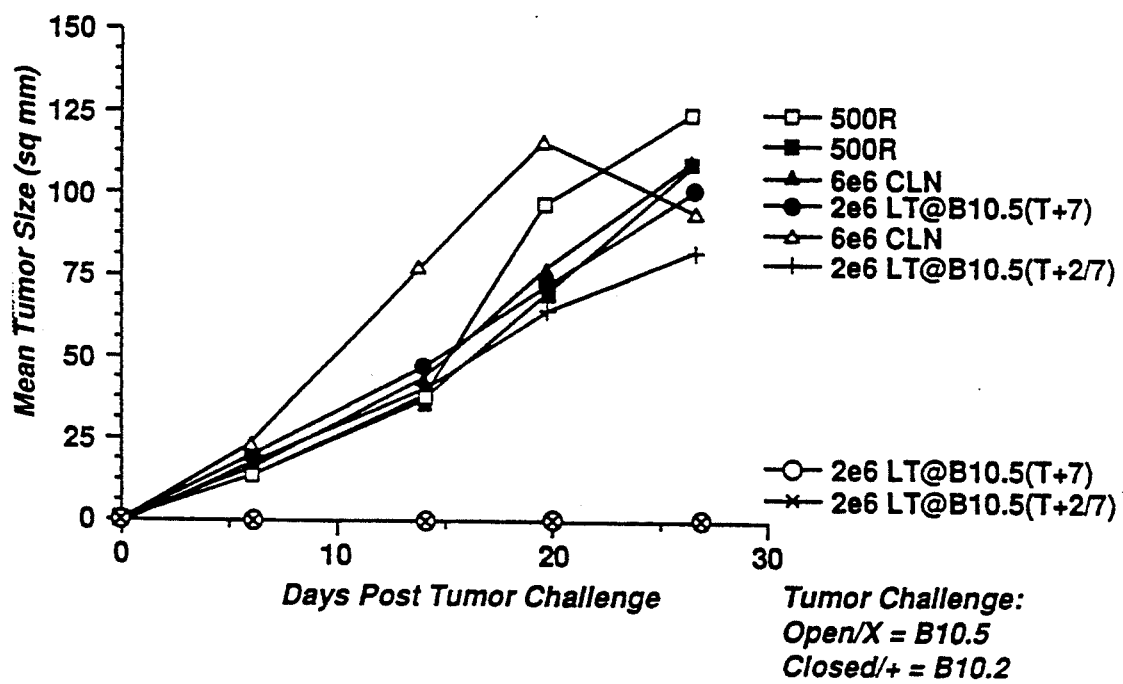

We determined whether DLN cells maintained in long term culture could mediate tumor rejection in vivo. Syngeneic B10 mice were irradiated with 500 rads. Long term (five weeks) cultures of DLN cells ($2 \times 10^6$ cells) were administered i.v. to the irradiated mice. Mice were challenged with $5 \times 10^5$ tumor cells administered by intradermal injection. Tumor growth was determined by measuring tumor size. Either B10.5 (specific) or B10.2 (non-specific) tumor cells were used for challenge. Only DLN cells that were maintained in culture medium having IL-7 were able to reject specific (i.e., B10.5) tumor challenge but not non-specific (i.e., B10.2) tumor challenge (FIG. 18). Additional presence of IL-2 in the culture medium did not serve as a detriment to the beneficial effects of IL-7.

These data demonstrate that therapeutically effective anti-tumor CTL activity can be maintained for extended periods of time (at least five weeks) ex vivo in culture medium containing either IL-7 alone or IL-7 in combination with IL-2. The most important component appears to be the inclusion of IL-7 into the culture medium because DLN cells cultured in medium containing IL-2 alone did not support lymphoid cell growth to an extent sufficient to be tested for in vivo immunotherapeutic efficacy.

What is claimed is:

1. An immunotherapy method for treating an individual with cancer that responds to immunotherapy and which is formed by specific tumor cells displaying a specific antigen, comprising:
   obtaining lymphoid cells exposed to the specific antigen;
   culturing the lymphoid cells ex vivo in a culture medium comprising an amount of an IL-7 polypeptide sufficient to induce CTL activity in the lymphoid cells; and
   administering the lymphoid cells displaying CTL activity to the individual.

2. The immunotherapy method of claim 1, further comprising administering an effective anti-tumor amount of an IL-7 polypeptide to the individual.

3. The method of claim 1 wherein the concentration of the IL-7 polypeptide in the culture medium is from about 2.5 ng/ml to about 20 ng/ml.

4. The method of claim 3 wherein the concentration of the IL-7 polypeptide in the culture medium is about 10 ng/ml.

5. The method of claim 1 wherein the culture medium further comprises an effective amount of a cytolytic stimulating agent selected from the group consisting of IL-2 polypeptides or derivatives thereof, IL-4 polypeptides or derivatives thereof, a population of mitotically inactivated specific tumor cells, and combinations thereof.

6. The method of claim 5 wherein the concentration of the IL-2 polypeptide or derivative thereof is about 2 ng/ml.

7. The method of claim 5 wherein the concentration of the IL-4 polypeptide or derivative thereof is about 5 ng/ml.

8. The method of claim 1 wherein the culture medium further comprises a population of mitotically-inactivated specific tumor cells.

9. A population of activated lymphoid cells for immunotherapy of cancer, comprising a culture of lymphoid cells surviving at least 10 days in ex vivo culture in the presence of at least 2 ng/ml of an IL-7 polypeptide; wherein the lymphoid cells display CTL activity characterized by CD8 positive T cells.

10. A population of activated lymphoid cells for adoptive immunotherapy of cancer formed by specific tumor cells displaying a specific antigen, produced by the process comprising:
    obtaining lymphoid cells exposed to the specific antigen:
    culturing the lymphoid cells ex vivo in a culture medium comprising an amount of an IL-7 polypeptide sufficient to induce CTL activity in the lymphoid cells.

11. The population of activated lymphoid cells of claim 10 wherein the concentration of the IL-7 polypeptide in the culture medium is from about 2 ng/ml to about 20 ng/ml.

12. The population of activated lymphoid cells of claim 11 wherein the concentration of the IL-7 polypeptide in the culture medium is about 10 ng/ml.

13. The population of activated lymphoid cells of claim 10 wherein the culture medium further comprises a population of mitotically-inactivated specific tumor cells.

14. The population of activated lymphoid cells of claim 10 wherein the culture medium further comprises an effective amount of a cytolytic stimulating agent selected from the group consisting of IL-2 polypeptides or derivatives thereof, IL-4 polypeptides or derivatives thereof, a population of mitotically inactivated specific tumor cells, and combinations thereof.

15. A population of syngeneic lymphoid cells for adoptive immunotherapy of cancer formed from specific tumor cells produced by the process comprising:
    obtaining syngeneic peripheral lymphoid cells; and
    culturing the syngeneic lymphoid cells ex vivo in a culture medium comprising an amount of conspecific IL-7 polypeptide sufficient to induce CTL activity in the lymphoid cells plus up to about 3 ng/ml of an IL-2 polypeptide or derivative thereof.

16. The population of syngeneic lymphoid cells of claim 15 wherein the concentration of the IL-7 polypeptide in the culture medium is from about 2.5 ng/ml to about 20 ng/ml.

17. The population of syngeneic lymphoid cells of claim 16 wherein the concentration of the IL-7 polypeptide in the culture medium is about 10 ng/ml.

18. The population of syngeneic lymphoid cells of claim 15 wherein the concentration of the IL-2 polypeptide or derivative thereof is about 2 ng/ml.

19. The population of syngeneic lymphoid cells of claim 15 wherein the culture medium further comprises a population of mitotically-inactivated specific tumor cells.

20. A method for forming a proliferated population of mammalian cytolytic T lymphocytes having lytic specificity for cells displaying a specific antigen, comprising contacting a T cell population previously exposed to the specific antigen with a culture medium comprising a biologically effective amount of an IL-7 polypeptide.

21. The method of claim 20 wherein the culture medium further comprises an IL-2 polypeptide or a derivative thereof.

22. The method of claim 20 wherein the concentration of the IL-7 polypeptide is from about 2.5 ng/ml to about 20 ng/ml.

23. The method of claim 22 wherein the concentration of the IL-7 polypeptide is about 10 ng/ml.

24. The method of claim 21 wherein the culture medium further comprises an effective amount of a cytolytic stimulating agent selected from the group consisting of IL-2 polypeptides or derivatives thereof, IL-4 polypeptides or derivatives thereof, a population of mitotically inactivated specific tumor cells, and combinations thereof.

25. The method of claim 20 wherein the specific antigen is a virus associated antigen or a tumor associated antigen.

26. An isolated population of activated mammalian cytolytic T lymphocytes having lytic specificity for cells displaying a specific antigen wherein the population of proliferated cytotoxic T lymphocytes is produced by an ex vivo process, comprising obtaining a lymphoid cell population exposed to the specific antigen, and contacting the lymphoid cell population with a culture medium comprising a biologically effective amount of an IL-7 polypeptide.

27. The isolated population of activated mammalian cytolytic T lymphocytes of claim 26 wherein the culture medium further comprises an IL-2 polypeptide or a derivative thereof.

28. The isolated population of activated mammalian cytolytic T lymphocytes of claim 26 wherein the concentration of the IL-7 polypeptide in the culture medium is from about 2.5 ng/ml to about 20 ng/ml.

29. The isolated population of activated mammalian cytolytic T lymphocytes of claim 28 wherein the concentration of the IL-7 polypeptide in the culture medium is about 10 ng/ml.

30. The isolated population of activated mammalian cytolytic T lymphocytes of claim 27 wherein the concentration of the IL-2 polypeptide or derivative thereof in the culture medium is about 2 ng/ml.

31. The isolated population of activated mammalian cytolytic T lymphocytes of claim 26 wherein the specific antigen is a virus associated antigen or a tumor associated antigen.

* * * * *

UNITED STATES PATENT AND TRADEMARK OFFICE
CERTIFICATE OF CORRECTION

PATENT NO. : 5,229,115
DATED : July 20, 1993
INVENTOR(S) : David H. Lynch It is certified that error appears in the above-identified patent and that said Letters Patent is hereby corrected as shown below:

```
Column  3, lines 32 & 33, "pharmacokinetics" should be --pharmacokinetic--.
Column  5, line 28, please delete first "were".
Column  9, line 5,  please delete first "in".
           lines 7 & 8, "compound" should be --compounds--.
Column 10, line 51, "commercially" should be --commercial--.
Column 12, line 59, "effect" should be --affect--.
Column 15, line 29, "Example" should be --Examples--.
           line 33, "cell" should be --cells--.
Column 17, line 44, "FIG. 14)" should be --(FIG. 14)--.
Column 19, line 45, after "polypeptide" the ";" should be a --,--.
           lines 52 & 53, after "antigen" the ":" should be a --;--.
```

Signed and Sealed this

Twenty-fourth Day of May, 1994

Attest:

BRUCE LEHMAN

*Attesting Officer*       Commissioner of Patents and Trademarks